US011538157B1

(12) United States Patent
Schoess et al.

(10) Patent No.: US 11,538,157 B1
(45) Date of Patent: *Dec. 27, 2022

(54) IMAGING SYSTEM AND METHOD FOR ASSESSING WOUNDS

(71) Applicants: Jeffrey Norman Schoess, Howard Lake, MN (US); David G. Armstrong, Studio City, CA (US)

(72) Inventors: Jeffrey Norman Schoess, Howard Lake, MN (US); David G. Armstrong, Studio City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/543,592

(22) Filed: Dec. 6, 2021

Related U.S. Application Data

(63) Continuation-in-part of application No. 17/005,257, filed on Aug. 27, 2020, now Pat. No. 11,195,281.

(60) Provisional application No. 62/867,693, filed on Jun. 27, 2019.

(51) Int. Cl.
| | |
|---|---|
| G06K 9/00 | (2022.01) |
| G06T 7/00 | (2017.01) |
| G06T 7/50 | (2017.01) |
| G06T 7/13 | (2017.01) |
| A61B 5/00 | (2006.01) |
| A61B 5/01 | (2006.01) |

(52) U.S. Cl.
CPC ............ *G06T 7/0012* (2013.01); *A61B 5/015* (2013.01); *A61B 5/4842* (2013.01); *G06T 7/13* (2017.01); *G06T 7/50* (2017.01); *A61B 2576/02* (2013.01); *G06T 2207/10048* (2013.01); *G06T 2207/30088* (2013.01)

(58) Field of Classification Search
CPC .................................................. G06T 7/0012
See application file for complete search history.

(56) References Cited

U.S. PATENT DOCUMENTS

| | | | |
|---|---|---|---|
| 2013/0116573 A1* | 5/2013 | Herman | A61B 5/444 600/474 |
| 2017/0296071 A1* | 10/2017 | Spahn | A61B 5/0261 |
| 2018/0046878 A1* | 2/2018 | Wang | G06V 10/44 |
| 2018/0098727 A1* | 4/2018 | Spahn | G06T 7/0012 |
| 2019/0021649 A1* | 1/2019 | Van Snellenberg | A61B 5/4041 |
| 2019/0125248 A1* | 5/2019 | Curtin | G06F 16/5854 |
| 2020/0085313 A1* | 3/2020 | Bunker | A61B 5/015 |
| 2020/0345295 A1* | 11/2020 | Swerdlow | A61B 5/7267 |

OTHER PUBLICATIONS

Aliahmad et al (NPL "Is Thermal Imaging a Useful Predictor of the Healing Status of Diabetes-Related Foot Ulcers?", Journal of Diabetes Science and Technology2019, vol. 13(3) 561-567) (Year: 2019).*

* cited by examiner

*Primary Examiner* — Oneal R Mistry
(74) *Attorney, Agent, or Firm* — Underwood & Associates, LLC

(57) ABSTRACT

A method for determining healing progress of a tissue disease state includes receiving a thermal image of a target wound area from a thermal imaging system, processing the thermal image to construct an isotherm map of at least one selected area, determining a thermal index value from the isotherm map, correlating the wound thermal index value with a reference thermal index value representative of an injury-free state.

17 Claims, 18 Drawing Sheets

IMAGING SYSTEM AND METHOD FOR ASSESSING WOUNDS

CROSS REFERENCE TO RELATED APPLICATIONS

This application is a continuation-in-part of U.S. patent application Ser. No. 17/005,257, titled "Imaging System and Method for Assessing Wounds" filed on Aug. 27, 2020, now U.S. Pat. No. 11,195,281, which claims benefit under 35 U.S.C. § 119(e)(1) to the filing date of provisional patent application Ser. No. 62/867,693 having the same title and filed on Jun. 27, 2019. Each of the foregoing provisional and non-provisional applications is expressly incorporated herein by reference.

STATEMENT REGARDING FEDERALLY SPONSORED RESEARCH OR DEVELOPMENT

This invention was made with government support under Grant No. 1R43DK10244 awarded by The National Institutes of Health and Phase II Grant No. 5R44DK102244 awarded by the National Institute of Diabetes and Digestive Kidney Diseases. The government has certain rights in the invention.

TECHNICAL FIELD

This disclosure relates to systems and methods for wound imaging. In particular, this disclosure relates to a wound imaging system for quantifying physiological aspects of a wound.

BACKGROUND

More individuals are now dying of chronic non-communicable diseases (NCD) than acute diseases associated with disasters, trauma or infection. Diabetes is a quintessential NCD. The prevalent and long-neglected diabetic foot ulcer (DFU), and the accompanying lower extremity complications of DFU, rank among the most debilitating and costly sequela of this syndrome in both the developed and developing world. Around the globe, diabetes results in one major limb amputation every 20 seconds, over 2500 limbs lost per day. In 2012, the total cost of diabetes was $245 billion, a 41% increase from 2007. In the US, one-third of diabetes-related costs are spent on DFUs. Two-thirds of these DFU costs are incurred in inpatient settings.

On a national average, it is estimated that emergency treatment of DFUs costs $1.9 billion per year and $8.78 billion per year for inpatient care for these patients. Arguably, the most significant consequence of DFUs is amputation, especially in the lower extremities, complicating more than 10% of cases. It is estimated that approximately 70% of such amputations are preventable. There is room for improvement in the effective management of DFUs, which could be addressed with better preventative and effective management measures. In particular, there is a significant gap in the management and measurement of ulcer recurrence, which is estimated to be between 30-40% in the first year following initial ulceration.

SUMMARY

In general, an imaging system applicable in, for example, but not limited to mobile health (mHealth) healthcare environments is disclosed. Certain advantages of the systems and methods include providing a communication and motivational strategy for patients during clinic visits through use of visual imagery, charts, trends and other data that aid in self-care and compliance; integration of wound care progress into electronic health records systems for research and other purposes; providing a reimbursement strategy for use of advanced therapies based on objective visual evidence collected; and integration of wound management in telecare or decision support systems, especially for remote patient monitoring (RPM) and virtual medicine. A related advantage includes the ability to communicate with patients visually, e.g., so as to be able to visualize clinical prognosis. This can provide a patient incentive for self-accountability and self-education in addition to predicting the likelihood of healing through patient behavior, among others.

In one exemplary aspect, a method for determining healing progress of a tissue injury is disclosed. The method includes receiving a thermal image of a target wound area of a living subject from a thermal imaging system, processing the thermal image to construct an isotherm map of at least one selected area of the target wound area, determining a thermal index value from the isotherm map, correlating the thermal index value with a previously-determined thermal index value representing a pre-existing pre-ulcerous, ulcerous-free, or ulcerous state of the target wound area to ascertain whether the tissue injury is progressing toward healing or degenerating, and transmitting the thermal index value to an output register.

In one embodiment, the thermal index value is representative of healing progress of the tissue injury. In one embodiment, the tissue injury is an ulcer.

In one embodiment, processing the thermal image includes converting the thermal image from a color image to a greyscale image, applying a digital filter to the greyscale image, applying a contour plotting algorithm to determine isotherms contained in the greyscale image and assigning a contour level value correlated to a measured temperature value of each isotherm and optionally assigning a visual identifier to each isotherm. Applying a digital filter to the greyscale image can include applying a Gaussian Blur filter.

In one embodiment, the method further includes decimating the bit depth of the thermal image.

In one embodiment, the step of determining a thermal index value from the isotherm map includes calculating $(\Delta T \cdot a)/A$, wherein $\Delta T$ represents the temperature difference between an isotherm of an ulcer within the target wound area and a mean temperature of surrounding ulcer-free tissue, a is the area of the isotherm in the target wound area and A is an area of a wound bed of the ulcer. In one embodiment, the thermal image is obtained by a thermal imaging camera, and the output register is configured to transmit the thermal index value to a remote computing system integral with a mobile health healthcare platform.

In another exemplary aspect, a method for determining a course of healing of a tissue injury is disclosed. The method includes a) receiving a thermal image of a target wound area; b) digitally processing the thermal image to create an isotherm map comprising a plurality of isotherms, the plurality of isotherms defining a region of interest of the target wound area; c) assigning a numerical index to each of the isotherms in the plurality of isotherms and calculating a thermal index therefrom; d) receiving a second, different and subsequent thermal image of the target wound area; e) repeating steps b) and c) with respect to the second thermal image; f) determining a course of healing by comparing differences between the thermal indexes of the first and the second thermal images; and g) transmitting the result of the determining step f) to an output register.

In one embodiment, the difference between the thermal indexes of the first and the second thermal images can indicate a positive healing trend, or a negative healing trend based on whether the calculated thermal index increases or decreases, respectively.

In one embodiment, digitally processing the thermal image to create an isotherm map includes converting the thermal image to a greyscale image, down-converting a bit depth of the greyscale image, applying a Gaussian Blur filter to the down-sampled image, and assigning a contour level value correlated to a measured temperature value of the isotherm and optionally assigning a visual identifier to each isotherm.

In one embodiment, the numerical index of each of the isotherms is correlated to a pixel-derived temperature value.

In one embodiment, the thermal image is obtained by a thermal imaging camera, and the output register is configured to transmit the thermal index value to a remote computing system integral with a mobile health healthcare platform.

In another exemplary aspect, a method for determining a course of healing of a ulcerative state in a living being includes selecting a target wound area comprising an ulcer, obtaining a thermal image of the target wound area, identifying one or more regions of interest within the target wound area and estimating the ulcerative state by determining a thermal index of the ulcer.

In one embodiment, the one or more regions of interest include hotspots indicating inflammation, or cold spots indicating ischemia, identified by the thermal image due to new ulceration, ulcer recurrence or tissue breakdown.

In one embodiment, the regions of interest include ulcer or peri-wound locations within the one or more regions of interest. In a related embodiment, the method further includes determining isotherms within a digitally-processed version of the thermal image. In a related embodiment, the digitally-processed version of the thermal image is obtained by gradient-based edge and contour plotting.

In one embodiment, the thermal index of the ulcer is determined by applying the equation $TI=(\Delta T*a)/A$, wherein $\Delta T$ represents the temperature difference between an isotherm of the ulcer within the target wound area and a mean temperature of surrounding ulcer-free tissue, a is the area of the isotherm in the target wound area and A is an area of the ulcer wound bed.

In one embodiment, the method further includes transmitting the thermal index value to a remote computing system integral with a mobile health healthcare platform.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings, which may not necessarily be to scale, in which like references indicate similar elements, and in which.

DETAILED DESCRIPTION OF ILLUSTRATIVE EMBODIMENTS

Figure 1:
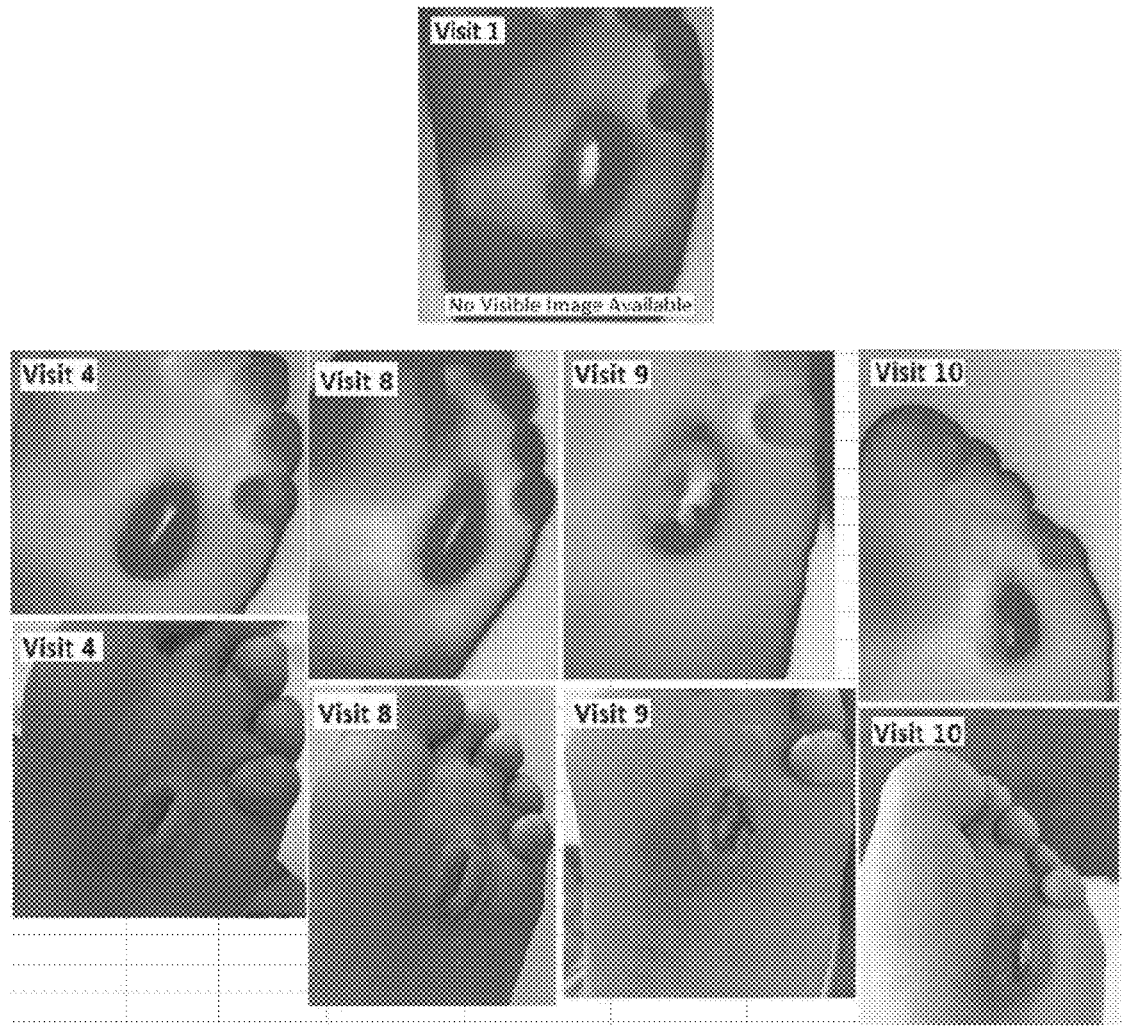
FIG. 1 is a series of images showing foot ulceration.

Qualification and quantification of wound size, shape, temperature distribution and surrounding tissue can predict the severity of a wound, provide insight into healing progress and predict reulceration in, for example, patents in diabetic foot remission. In a general aspect, the systems and methods described herein can provide a predictive association between properties of wounds captured through optical means such as photography and videography and the healing of the wound. Wound properties can include, for example, and without limitation, wound size (e.g., surface area), wound color, wound morphology (e.g., depth and shape of a wound bed), wound fluid types and temperature. Such properties can be captured by photographic methods, including, but not limited to the use of cameras, including cameras configured to collect light in a selected region of the electromagnetic spectrum, such as all or portions of the normal color spectrum, all or portions of the infra-red, visible and near-infra-red spectrum, etc. The collected images can be analyzed, transformed or manipulated so as to focus on certain portions of anatomy, including wound beds. A handheld portable device (referred to herein as Infrared Eyes, 'iREyes') for accurately measuring wound size, temperature and other wound aspects is disclosed, which can be implemented, e.g., in mobile health (mHealth) environments.

mHealth environments provide advantages of reduced workflow and reduced manual labor, the ability to be easily and directly integrated with electronic health records (EHR) services, the provision of a more objective and quantitative assessment of wound conditions, and the flexibility of being used in clinical, veterinary, health and wellness and other applications. In one approach, thermal imagery of wounds and surrounding tissue can be used for diagnostic purposes; visible imagery can be used for identifying regions of interest (ROI) (e.g., a region where conditions may exist of a pre-existing wound, existing wound or area of potential ulcer recurrence) wound area, etc.; however, combinations of thermal and visible imagery can be used in various cooperative quantitative and qualitative approaches to wound care and management.

For example, thermal images of wounds and surrounding healthy tissue can present regions of differing temperature, referred to "hot" or "cool/cold" spots. Such areas can be analyzed as a sub region of interest (ROI) or isotherm pattern within the thermal image. Isotherms can manifest directly from thermal images or, in some embodiments, thermal images can be processed by software to create isotherms overlaid on the image and can assist in determining the location of hot or cool/cold spots. An isotherm is defined as a 3-dimensional map of thermal imagery that indicates the series of contour lines having the same temperature at a given time. The isotherm defines a temperature profile of how the hot- or cold spot is depicted or illustrated.

In one approach, ROIs can manifest isotherm features that can be useful for clinical diagnosis. Such features include, for example, and without limitation: the isotherm shape (e.g., round, oblong, irregular); the number of thermal contour levels (e.g., distinct levels of temperature variation, and temperature range) per isotherm; a contour gradient factor (e.g., increase or decrease between contour levels indicating temperature increase or decrease); and a contour line density/spacing factor.

In one embodiment, a hot spot can be defined as sub-ROI with a center region as the highest temperature, with cooler temperatures surrounding it indicated by contour levels surrounding the center region, with each contour level at a fixed temperature, with decreasing fixed temperatures at each level.

In one embodiment, a cool- or cold spot can be defined as a sub-ROI with the substantially opposite thermal pattern of a hot spot, with a cool center region surrounded by bands (e.g., contour levels) of increasing temperature.

In one embodiment, quantification of certain wound parameters (such as inflammation) can be expressed as a thermal index TI, where $TI=(\Delta T*a)/A$. In this equation, $\Delta T$ represents the temperature difference between an isotherm of the wound and a mean foot temperature; a is the area of the isotherm in a wound area and A is an area of the wound bed. The thermal index can be used to aid in clinical or self-diagnosis, such as to assess or classify wounds (e.g., according to their urgency or need for medical intervention or treatment) and to both qualitatively and quantitatively measure wound healing over time.

Such an approach can provide a novel clinical practice guideline based on objective evidence, that can aid clinicians in providing appropriate interventions in addition to the standard of care for diabetic foot wounds, in particular, which can be stratified based on healing trajectory and risk assessment though routine thermal imaging. This can afford better evidence-based regulation of pharmacological and device (bio-engineered tissues, wound dressings) interventions for wound healing.

In one example, the systems and methods described herein can be used for predicting the development of a new wound (preventive care) due to subdermal trauma, the risk of ulcer recurrence, predicting the healing path of an existing wound (i.e. a diagnosis) or a combination thereof. Subdermal trauma is typically generated by repetitive stress applied to foot tissue over a bony prominence (e.g., metatarsal head). For example, as a patient is admitted into the hospital or other care center, a scan can be performed to determine an amount of tissue breakdown in the areas of greatest concern. A scan using iREyes can suggest that if the likelihood of skin breakdown down is imminent, then appropriate action can be taken, e.g., identifying additional resources needed for that patient (specialty off-loading devices, specialty beds, etc.). The early detection of ulcer recurrence can provide 'ulcer-free' days to reduce patient follow-up care and hospitalization costs. Such information can aid the patient in, e.g., realizing hospital costs up-front. Additionally, a likelihood of skin breakdown may be fed into the patient's history to document that when the patient arrived the likelihood to skin breakdown down and associated wound development was high, because the skin had already moved to this level before the patient arrived. The systems and methods described herein can be used as a protective analysis tool, so if the patient develops wounds while in the hospital, it can be shown that appropriate steps were taken to prevent it. This can significantly reduce the number of lawsuits hospitals and skilled nursing facilities incur, providing a significant savings.

For example, this approach can be used for the identification of preulcerative damage to the plantar tissue of the feet. Regular monitoring of foot temperature has been demonstrated to be predictive of forthcoming DFU (Frykberg R G, Gordon I L, Reyzelman A M, Cazzell S M, Fitzgerald R H, Rothenberg G M, Bloom J D, Petersen B J, Linders D R, Nouvong A, Najafi B: *Feasibility and efficacy of a smart mat technology to predict development of diabetic plantar ulcers*. Diabetes Care 2017; 40:973-980), and can be used to warn individuals to decrease their physical activity engagement to lessen their likelihood of developing a DFU (Lavery L A, Higgins K R, Lanctot D R, Constantinides G P, Zamorano R G, Athanasiou K A, Armstrong D G, Agrawal C M: *Preventing diabetic foot ulcer recurrence in high-risk patients: use of temperature monitoring as a self-assessment tool. Diabetes Care* 2007; 30:14-20.).

The general premise to these interventions is that an inflammatory response is initiated in foot regions that are subjected to excessive physical stress. If a specific site on one foot is warmer than the equivalent location on the contralateral foot, the warm site can be reflective of preulcerative inflammation. For example, a 2.2° C. (4° F.) criteria is referred to as a threshold temperature, related to the asymmetry between the two feet, or a "temperature asymmetry threshold". In order to halt ulcer progression, patients can be advised to reduce their physical activity if they note a "hot spot." Once temperatures normalize between the two feet, patients are able to resume their normal activities. The importance of adherently measuring temperatures was highlighted by a 2007 study (Lavery et al., ibid.) It found that 80% (4/5) of participants who developed a DFU after being assigned to a temperature monitoring group did not comply with measuring their foot temperatures. More recently, a telemedicine system utilizing a floor mat with embedded temperature sensors was evaluated (Frykberg R G, ibid.). This system was designed to require no configuration or setup by the users who simply had to step on the mat with both feet for ~20 s. The system then compared the temperature profile of the two feet. Using a threshold of ≥2.22° C. difference between corresponding sites on opposite feet, the mat correctly predicted 97% of DFU with an average lead time of 37 days.

In one embodiment, an imager capable of collecting images of wounds and surrounding tissue includes, but is not limited to an infra-red imager, itself including, but not limited to an infra-red camera, a display driver, a touch-screen driver configured to receive user input and display images and output, a webcam and a control board providing logic instructions and circuitry for carrying out infra-red photography of chosen anatomical feature(s). One such imager is described in U.S. patent application Ser. No. 13/821,115 by Bharara et al., which is expressly incorporated by reference in its entirety herein.

Referring now to Table 1, quantified wound healing utilizing thermal indexing is shown. In this example, the test population included 17 DFU subjects including eleven males and six females: six were Latino, two were African American, one was Native American, six were Caucasian and one was of an unspecified ethnicity. There were sixteen Type 2 diabetics and 1 Type 1 diabetic subject. The subjects' ages ranged from 33 to 70 years old. Eleven of the seventeen subjects (64.71% of test population) had multiple clinical visits with wound index correlation showing an indication of wound healing process or delayed wound healing. Two of the subjects healed completely during the course (Subject Nos. 005 and 012), representing 11.76% of the test population. Five of the subjects were treated over a 15 week period or longer (subjects 001, 002, 004, 005, 011). Two types of wound healing patterns were observed during the study: a negative-to-positive index and a positive-to-negative index with both patterns trending to a final index value of zero as healing was occurring. Subjects 001, 002, 004, 005 and 017 were negative-to-positive indexes, and subjects 006, 009, 011, 012, and 013 were positive-to-negative indexes. The negative-to-positive index pattern typically involved isotherms in the wound-bed that would be warm at the beginning of the healing process and continue to be warm. The positive-to-negative index had isotherms that were cold and switched to being warm later in the healing process. Without wishing to be bound by theory, the positive-to-negative index may be an indicator of an ischemic condition for the patient.

Figure 2:
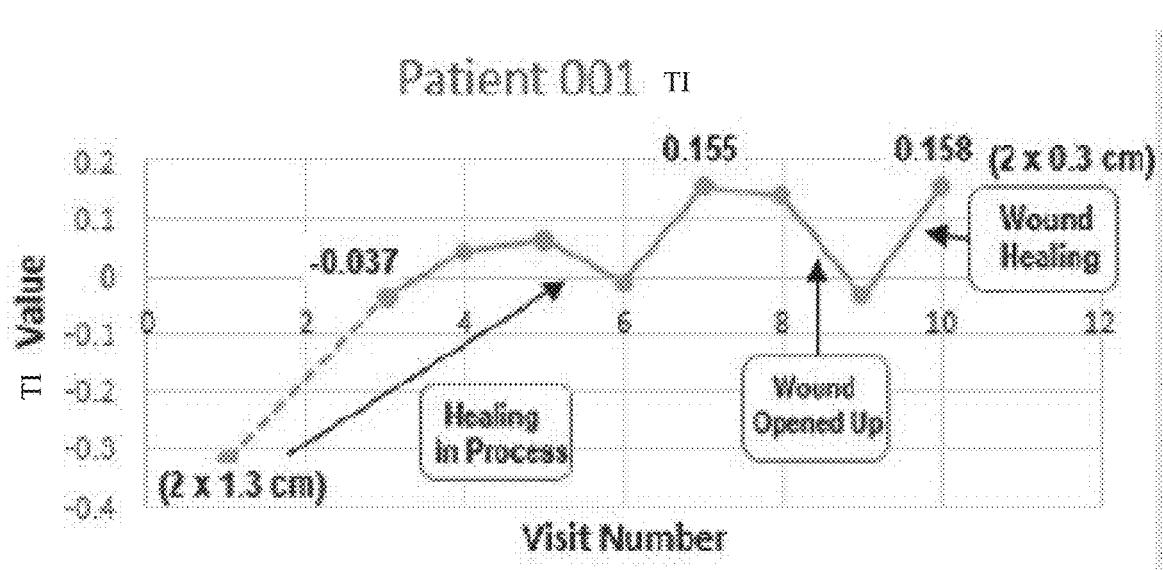
FIG. 2 is a plot of TI value vs. visit number.

Continuing this example and referring to Table 2 and FIGS. 1 and 2, Subject 001 was a 33 year old Type-2 diabetic male with a mid-left plantar ulcer with neuropathy. The subject had osteomyelitis, depression, bipolar (type 1 disorder) and existing left distal hallux wound as risk factors. His wound was treated over a 17 week period comprising 10 visits. The ulcer measured 2.3 cm×2.0 cm on the first visit, which was reduced to 2.0 cm×0.3 cm by the tenth visit. The wound edges were thickened and macerated with a light amount of serous fluid present. The wound was debrided with Gentian violet, packed with Acticoat 7, covered with Cutimed Soract, ABD pad and a wrap-style bandage. The subject's TI index indicated a clear course of healing (index of −0.318 to 0.158). The TI score tracked with the closure of the wound trending as a positive index until visit No. 9 when the wound opened, indicating a (−) index value. The wound had started to close again at visit No. 10, and healing progressed, as indicated by the TI index positive index score.

Figure 3:
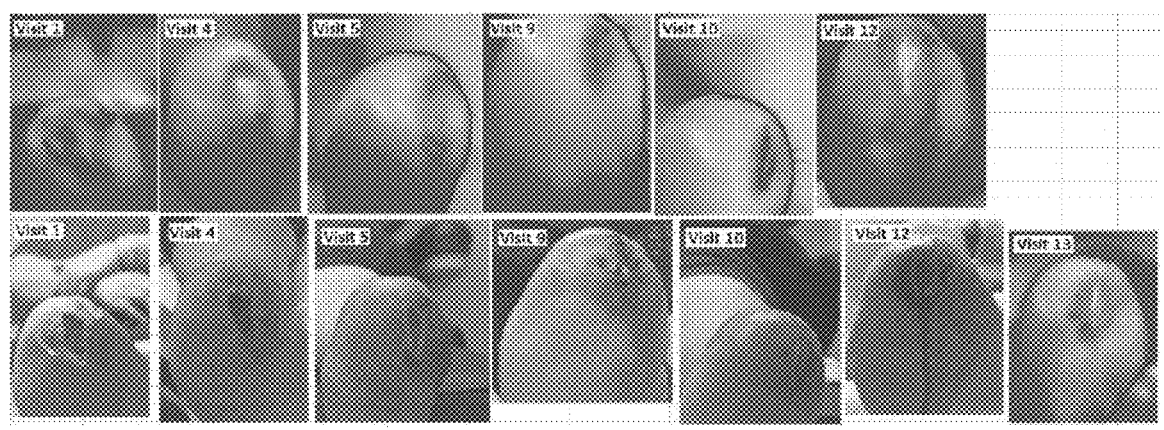
FIG. 3 is a series of images showing distal ulceration of the left leg.
Figure 4:
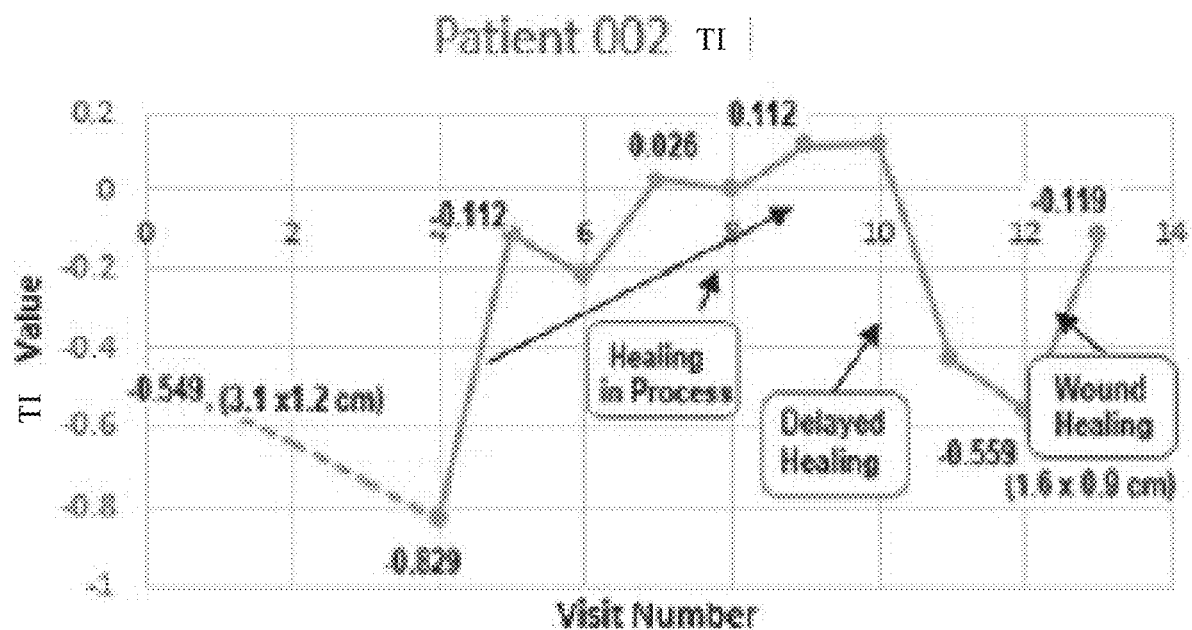
FIG. 4 is a plot of TI value vs. visit number.

Continuing the present example and referring to Table 3 and FIGS. 3 and 4, Subject 002 was a 41 year old Latino woman with a distal ulcer on the left leg following trans-metatarsal amputation (TMA). She was a type 2 diabetic and with neuropathy. The subject's other conditions included chronic kidney disease, sleep apnea, hypertension and chronic renal failure as risk factors. Her wound was treated over a 5 month period comprising 12 visits. The subject's wound measured 3.1 cm×1.2 cm at the first visit which reduced to 1.6 cm×0.9 cm at the $12^{th}$ visit. The subject's wound was debrided and treated with a negative wound pressure therapy vacuum, cast padding and a bandage wrap. Referring to FIG. 4, the subject's TI index indicated a clear course of healing (TI index of −0.549 to −0.119) during 2016-2017, respectively. Referring to FIGS. 3 and 4, the subject's TI score tracked with the closure of the wound, trending as a positive index, until visits 11 and 12. The wound was sutured earlier in visit 9. The wound reopened (visit 12) and started to heal again as evidenced in visit 13 as indicated with a positive TI score (0.559 to 0.119).

Figure 5:
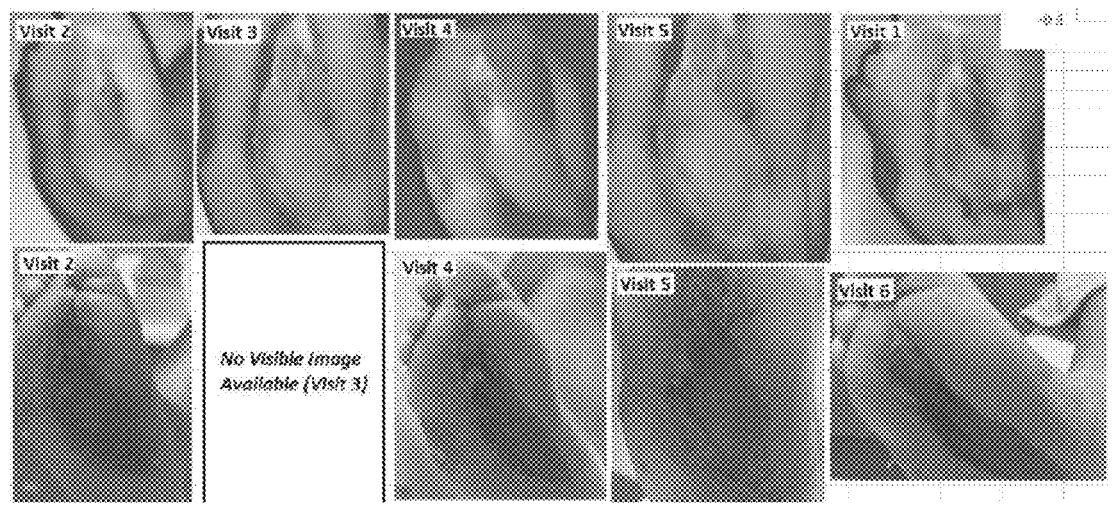
FIG. 5 is a series of images showing foot ulceration.
Figure 6:
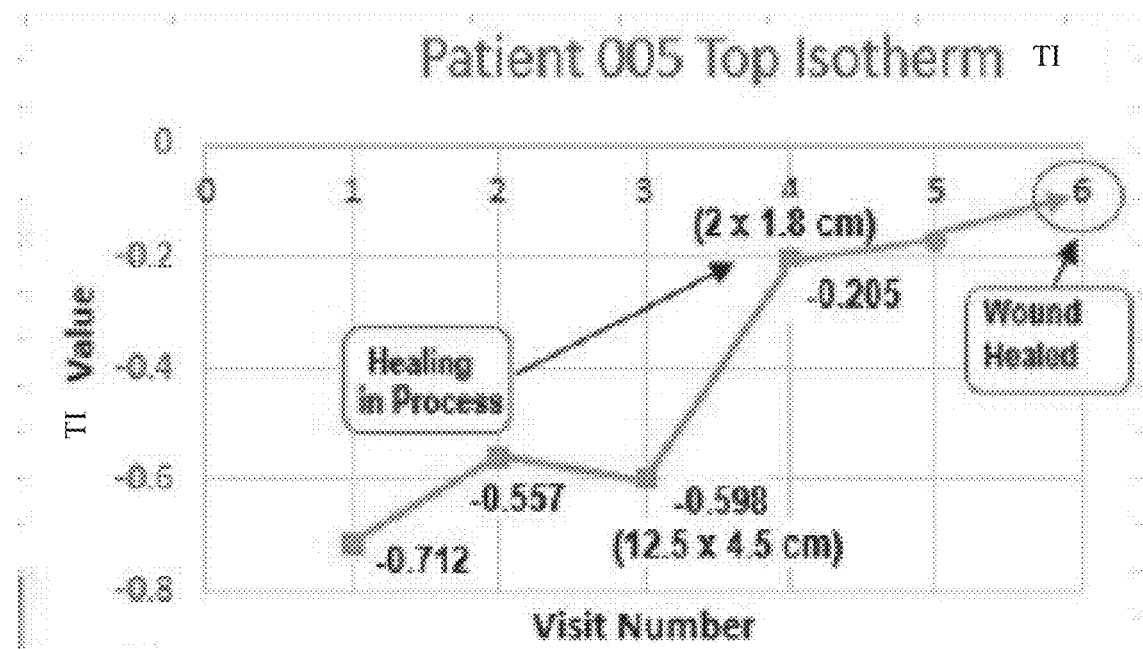
FIG. 6 is a plot of TI value vs. visit number.

Continuing the present example and referring to Table 4 and FIGS. 5 and 6, Subject 005 was a 43 year old African American female with a right lateral wound (STSG site). She is a type 2 diabetic with hypertension, MSRA, a second existing lateral 5th MTH wound and pancreatitis as risk factors. The subject's wound was treated over a 15 week time period, with the wound measuring 13.5 cm×1.0 cm (10.12 $cm^2$) on the first visit 1 to clinically healed state by the sixth visit. The peri-wound (tissue surrounding the wound) edges were thickened, with light serous-sanguineous drainage. The subject was treated with Dakins® solution, an ABD pad, cast padding and a bandage wrap. The subject's TI index indicated a clear course of healing, following an index of −0.712 on the first visit to −0.170 by the sixth visit.

Figure 7:
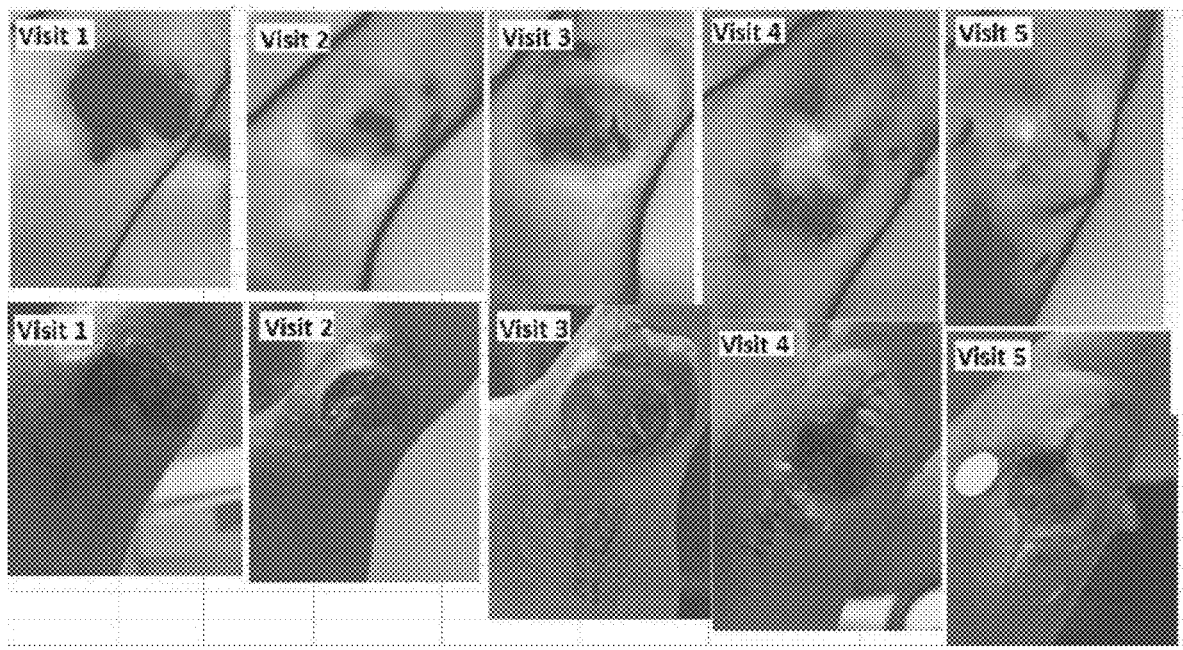
FIG. 7 is a series of images showing foot ulceration.
Figure 8:
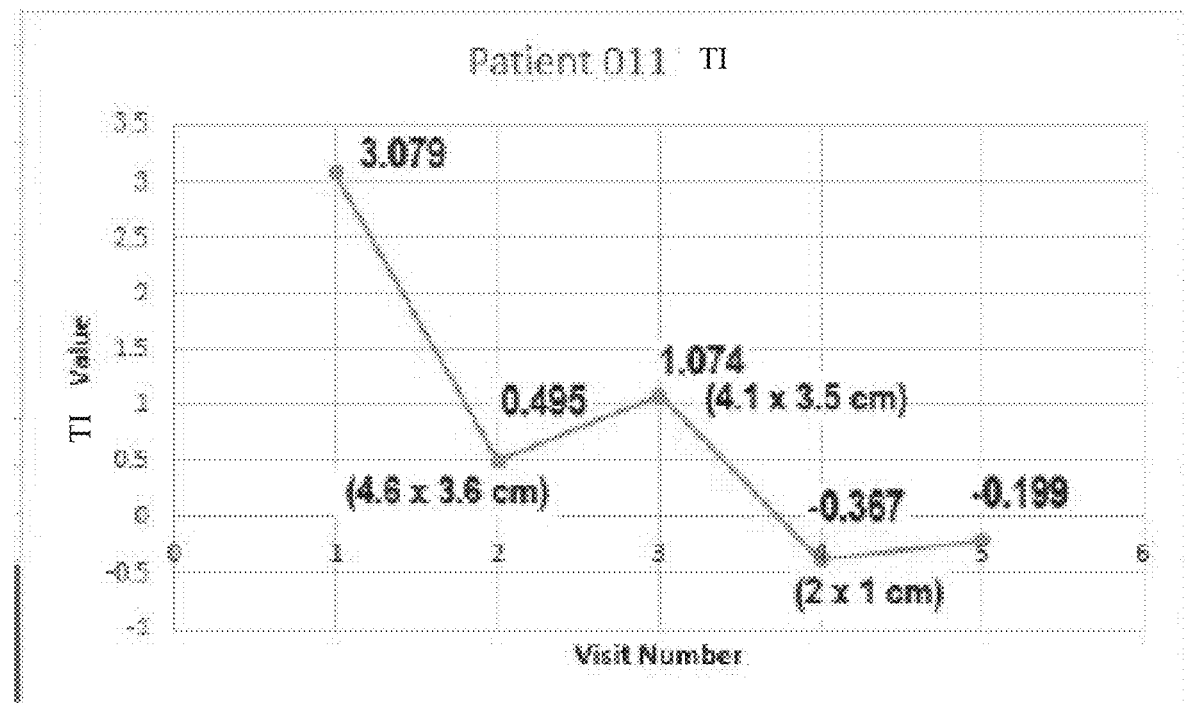
FIG. 8 is a plot of TI value vs. visit number.

Continuing the present example and referring to Table 5 and FIGS. 7 and 8, Subject 011 was a 47 year old Caucasian male with a lateral midfoot ulcer on his right foot. The subject was a type 2 diabetic with neuropathy, hypertension, Charcot, chronic osteomyelitis, and history of DFU as risk factors. The subject's wound was treated over 3 months comprising 5 visits, wherein the wound measured 6.0 cm×3 cm on visit 1; 3.6 cm×4.6 cm on visit 2; 3.5 cm×4.1 cm on visit 3; 4 cm×3.5 cm on visit 4; and 2.9 cm×2.8 cm on visit 5. The subject's wound base was fibrotic, showing islands of hypergranular tissue with a hyperkeratotic border, serous-sanginous drainage and no odor. No undermining or tunneling was noticed. The subject was treated with a suture closure on visit 4, debridement, Acicoat®, cast padding and an off-loading shoe. Referring to Table 5 and FIGS. 7 and 8, the subject's TI index indicated a clear course of healing, the TI index progressing from 3.079 to −0.199 with a negative-to-positive thermal index pattern.

Wound Healing Assessment Study Via Thermal Indexing

Figure 9:
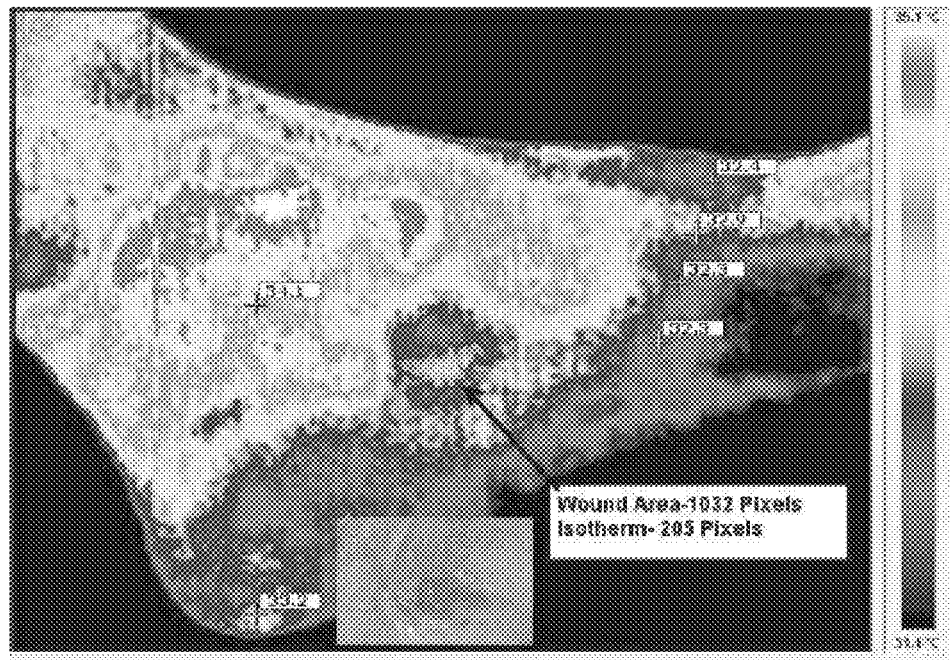
FIG. 9 is a thermal image of a foot.
Figure 10:
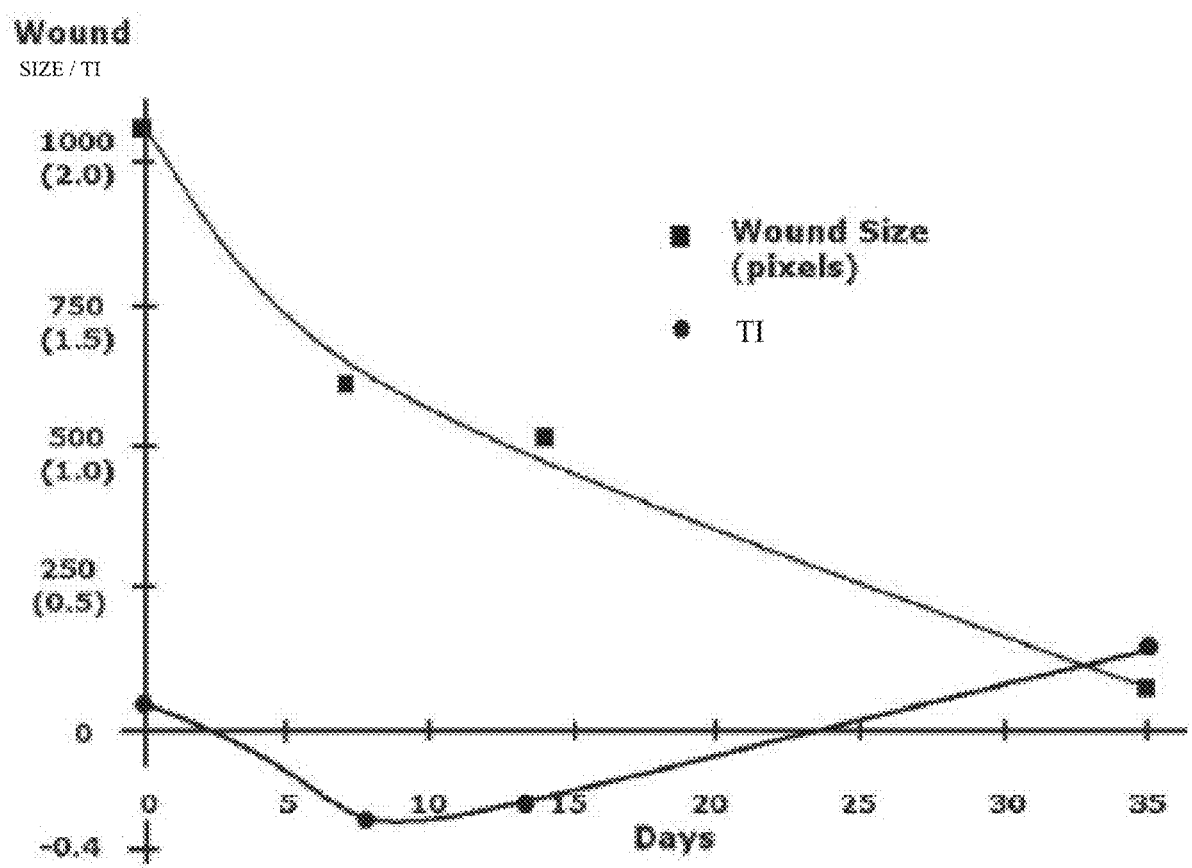
FIG. 10 is a plot of wound size/TI vs. days.

Referring now to FIGS. 9 and 10, and Table 6, a wound healing assessment study was conducted to provide clinical evidence of thermal indexing for wound healing. Three Type 2 diabetic test subjects were enrolled in the study and were followed serially over several weeks. Digital and thermal imaging were performed over a 35 day period for subjects Nos. 1 and 3, and 28 days for subject No. 2 (Table 6). FIG. 9 shows the study ulcer for test subject No. 1, who was a 71 year-old male with osteomyelitis at initial presentation (Day 0).

The thermal image reveals a circular-shaped wound area with a temperature range of 31.4 to 35.1° C. The visual image of the wound bed is also shown (see insert photo) for comparison with the thermal image. The wound area was measured to be 1032 pixels and the isotherm area to be 205 pixels. The average foot temperature was 32.87° C. (average of metatarsal heads no. 1 to 4, heel and ankle) and the average wound bed temperature was 33.3° C. A series of images were collected at Days 0, 7, 14, and 35 to evaluate the wound thermal index. FIG. 10 shows a graph of the wound size and thermal index for Subject No. 1, which correlates to the physiological healing progress of the wound.

Continuing with this example and referring in particular to Table 6, test subject 2, a 61 year-old male, and test subject 3, a 71 year-old male presented with right lateral foot ulcers. Utilizing the same or similar measurement techniques, similar changes in thermal index values were realized for each subject over a period of 4-5 weeks. In each case, the thermal index value shifts from negative to positive as wound healing occurs, which supports clinical pathological changes before they result in ulceration.

In this example, whole-foot skin temperatures are measured using a high-resolution, uncooled IR camera (FLIR Thermcam E4, FLIR Systems, Inc., Wilsonville, Oreg., U.S.A.) and a visible spectrum camera (Panasonic DMC-TZS, Panasonic Corp. of North America, Newark, N.J., USA). Without wishing to be bound by theory, it is suggested that early detection of damaging inflammation can be realized by monitoring a wound's thermal index for a positive-to-negative shift and associating the temporal behavior of TI (quantified during wound healing) with 4° F. clinical monitoring criteria (Armstrong D G, Holtz-Neiderer K, Wendel C, Mohler M J, Lavery L A, "Skin Temperature monitoring reduces the risk for diabetic foot ulceration in high risk patients", *AM J Med.* 2007:120(12):1042-6).

In one embodiment, thermal images of a wound and surrounding tissue can be captured using a mounted thermal camera. In certain embodiments, the camera can be mounted on a movable platform connected to a track. The camera can be moved while simultaneously collecting multiple images as the platform traverses the track, thereby providing for three-dimensional image captures after the multiple images have been processed.

Figure 11A:
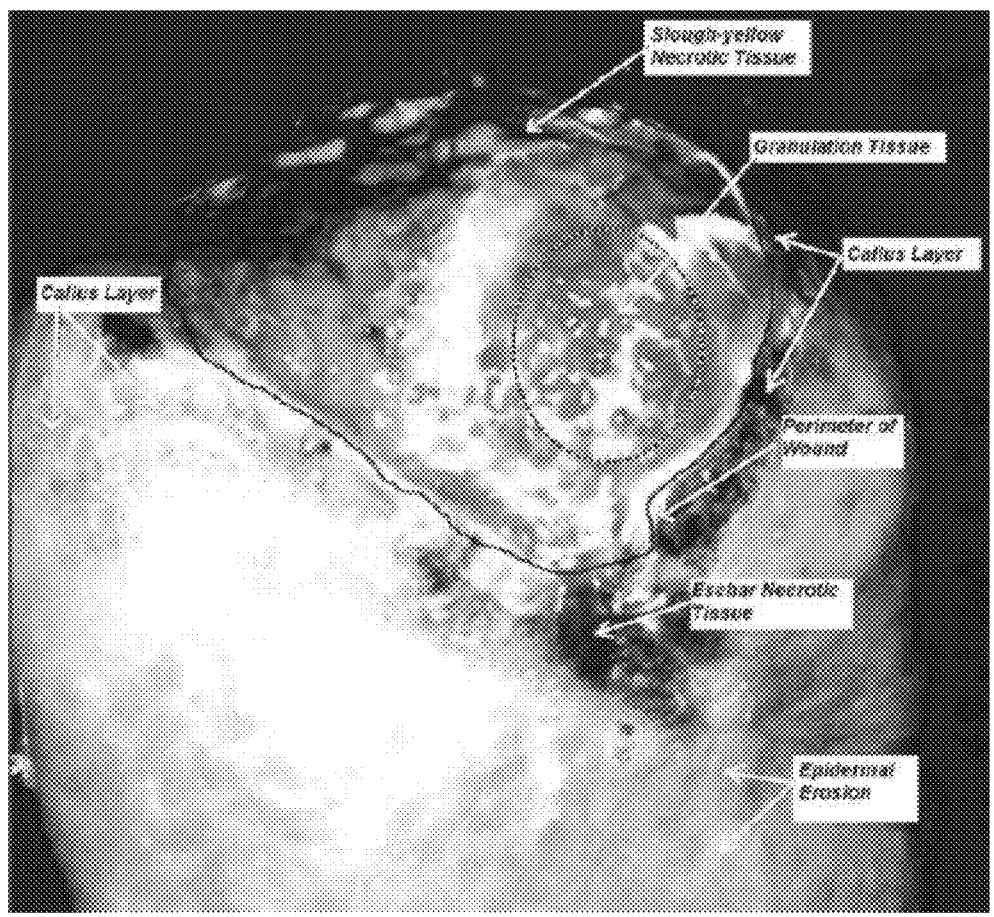
FIG. 11A is an image of a foot with granulation tissue formation, callus around the perimeter of a wound and necrotic tissue.
Figure 11B:
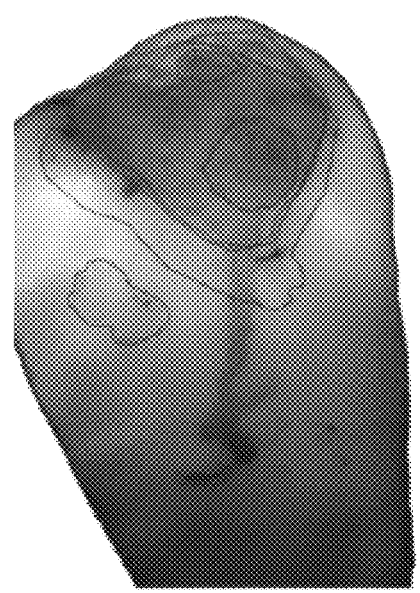
FIG. 11B is a grayscale infrared image of the foot shown in FIG. 11A.
Figure 11C:
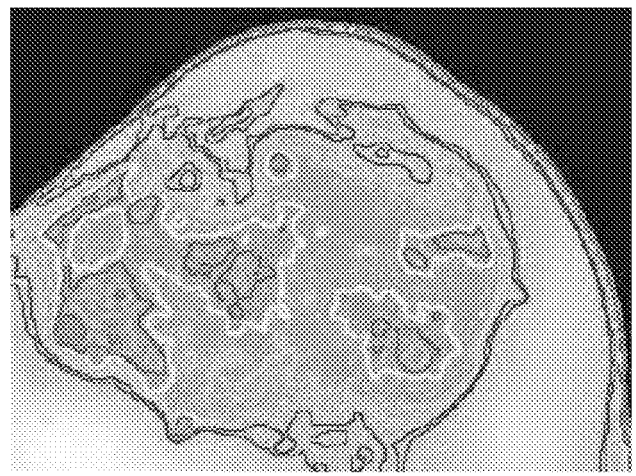
FIG. 11C illustrates ROI's in the wound bed indicating areas of inflammation in the infrared image, where tissue granulation may be occurring, according to one embodiment.
Figure 11D:
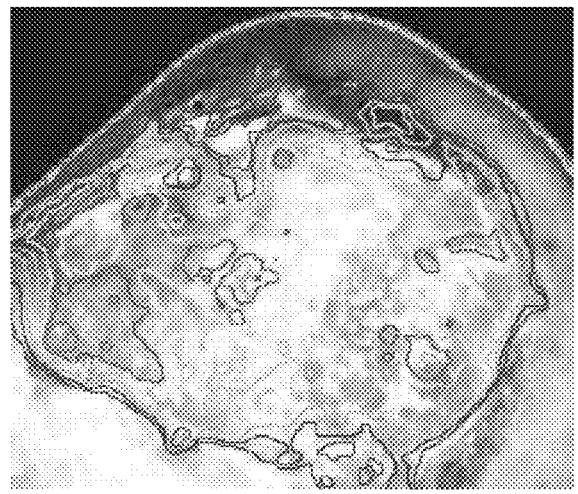
FIG. 11D is an infrared isotherm contour overlaid on a visible light image to correlate visible and thermal features of the wound and facilitate wound diagnostics, e.g., wound index estimation, according to one embodiment.

For example, referring to FIG. 11A, a labeled visible light image of a 45 year-old Native American with diabetes, peripheral neuropathy and a bilateral toe amputation. The patient's right foot is shown with granulation tissue formation, callus around the perimeter of the wound and necrotic tissue. FIG. 11b shows background subtraction is achieved for a grayscale infrared image with a combination of image filtering, edge detection and thresholding to construct a binary mask; FIG. 11C illustrates ROI's in the wound bed indicating areas of inflammation in the infrared image, where tissue granulation may be occurring; FIG. 11D shows the infrared isotherm contours overlaid on the visible light image to correlate visible and thermal features of the wound and facilitate wound diagnostics, e.g., wound index estimation.

Exemplary Camera System

Figure 12:
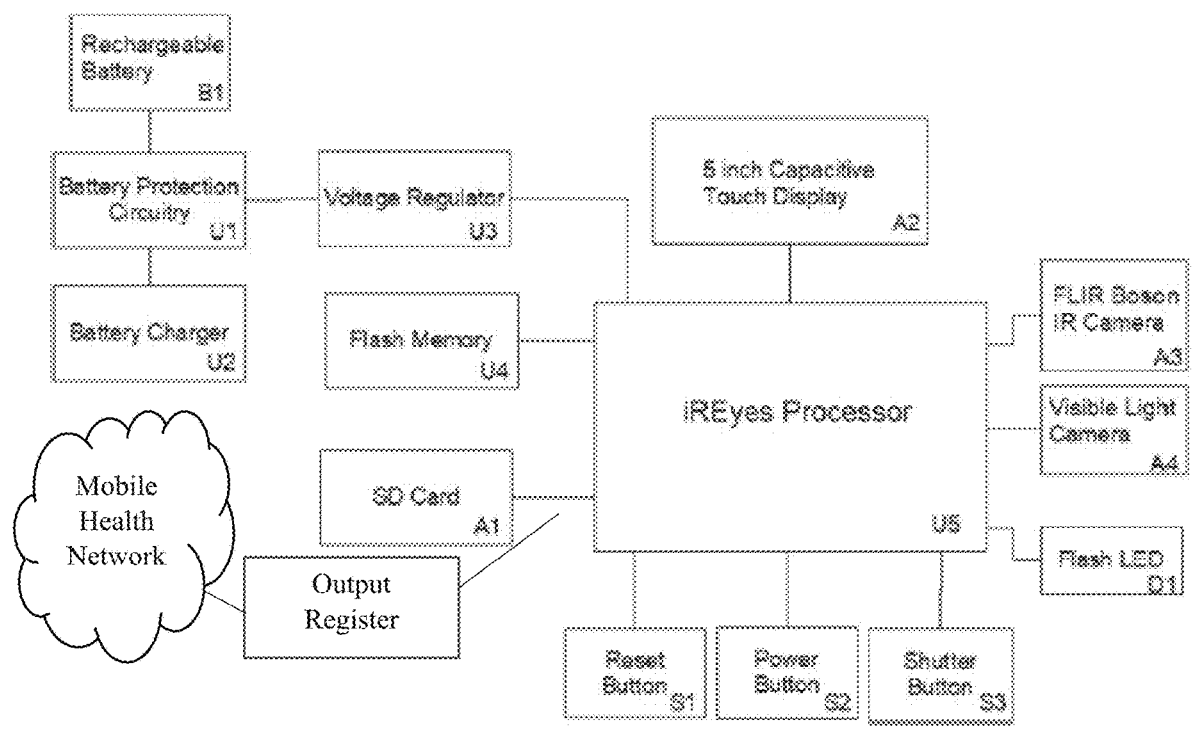
FIG. 12 is a schematic representation of a thermal imaging camera, according to one embodiment.

Referring now to FIG. 12, in one embodiment, a thermal imaging camera includes a processing unit (U5) which can include a microprocessor configured to carry out functions for imaging, analysis and other functions as described herein. The processing unit U5 can be configured for receiving input and output instructions, e.g., through the use of push-buttons (e.g., Reset button S1, Power button S2 and Shutter button S3) or other inputs, controlling an output display, capturing images, providing a user-navigable control menu and other functions. The processing unit U5 can also control a graphical user interface and image processing requirements.

In this embodiment, the camera utilizes a power system including a rechargeable battery (B1), circuit protection (U1), a battery charger (U2), and a voltage regulator (U3). In this example the charging circuitry regulates the current to the battery cell to properly charge the cell according to recommended charging curves. The protection circuitry protects the battery from short circuit conditions, over charging, over discharging, and limits the output current. The voltage regulator provides a constant DC voltage to the rest of the circuit components, which can be required due to the battery voltage output changing as the cell discharges. In this embodiment, the camera utilizes a FLIR Boson (A3) infrared imaging module configured to produce temperature information in the form of thermal images. An OEM-ready module can include a visible-spectrum camera, e.g., the Omni Vision Camera Cube which has a requisite resolution, a small form factor, and low cost than some other commercial products. The system can be battery powered, and mobile-health-ready by utilizing networking components and communications protocols known in the art. For example, the output register can be a network output port that is in signal communication with a network, e.g., the Internet, including a mobile-health network in signal communication with the Internet.

Still referring to FIG. 12, in this embodiment, the Boson is connected through a USB interface to the processor U5, which is configured to provide command and control functions of the system as well as the video stream. The visible light camera A4 can be a standard camera which outputs images in the visible spectrum range. The visible light camera is connected either through MIPI serial or USB. A 5-inch capacitive touch display A2 displays a user interface for inputting command and control functions in a GUI and is also configured to display captured images. The touch display includes a capacitive-touch sensitive overlay for navigating the GUI.

In this embodiment, the video display is connected through a 24-bit parallel interface, and the touch screen is connected through I2C. Flash LEDs D1 illuminate the target object for visible spectrum images and are selectively controlled by a dedicated flash driver integrated circuit. Flash memory U4 provides on-board memory storage for images and information, as well as the operating system. The interface to the flash memory can be, e.g., I2C or SPI. An SD Memory Card A1 expands the flash memory, increasing the available storage for saved images. In this embodiment, the SD card is connected via the SDXC interface.

In this embodiment the reset button S1, power button S2, and shutter button S3 allow user inputs separately from the touch screen, which are monitored by the processor through GPIO pins.

In this embodiment, the system can utilize, e.g., a Boson longwave infrared (LWIR) camera (FLIR, Willsonville, Oreg.). Such a camera can provide an expandable infrared video processing architecture, advanced image processing, video analytics, peripheral sensor drivers, and several industry-standard communication interfaces while keeping power consumption low. The system can utilize a visible light camera cube, for example, model no. OVM7690 provided by OmniVision Tech, Inc., Santa Clara, Calif., USA) can provide the functionality of a single chip image sensor, embedded processor and wafer-level optics in a low profile package (2.5 mm×2.9 mm×2.5 mm) capable of operating at up to 30 frames per second (fps) in VGA resolution with user control of image quality, formatting and output data transfer. Enabling output of 640×480 pixels allows users to perform image stabilization functions with post processing. All required image processing functions, including exposure, gamma, white balance, color saturation and hue control can be programmable through the camera interface.

Camera Optics

In one embodiment, the optical design incorporates a preferred lens; without limitation, it has been found that, for this embodiment, an optimal lens configuration for the Boson imager are a 4.3 mm lens with a field of view (FOV) of 50°, a 6.3 mm lens with an FOV of 34°, and a 9.1 mm lens with an FOV of 24°. For a target size of 12 inches, the lens configuration may require that the target be placed at 12.9 inches, 19.6 inches, and 28.2 inches, respectively. Thus, implementing a 6.3 mm lens can enable the imager to capture the entirety of a 12-inch foot at a convenient distance of 19.6 inches. Imaging a vertically oriented 12-inch long target with the vertically oriented 320×256 detector array implies a resolution of 0.9525 mm per pixel.

The imager can be positioned about 19.6 inches from the foot. After positioning the foot in the imager's field view, the focal length distance between the imager and the target can be adjusted by moving the imager back and forth slightly to obtain a clearly focused image. This approach achieves a field of view of 12 inches×9.6 inches which is sufficient to encompass the entirety of both feet for the vast majority of subjects.

In one embodiment, a camera of the type described herein can be integrated into a system for analyzing wound healing as described herein. For example, the Boson IR imager, processor module, flash memory, capacitive touch display, visible light camera, wireless communications, illumination LEDs and battery management can be integrated into a lightweight, 3-D printed thermoplastic housing to simplify manufacturing and significantly reduce product cost. A processor module with wireless support, battery management, flash memory, SD card support, and flash LED can be assembled on a surface-mount printed circuit board. A 3-D printed housing can be fabricated and assembled to contain these and other components. An optics alignment block can be used to provide proper alignment between the infrared and visible light cameras in the field-of-view. A 3.7-volt lithium-ion battery, for example, can be used to power the system. The processor module and alignment block can be mounted in the housing and connected together via a dedicated wire harness. After the imager is assembled the hardware and software integration process can occur incorporating software drivers for the display, flash memory, Boson camera and visible light camera.

Image Processing and Algorithm

Figure 13:
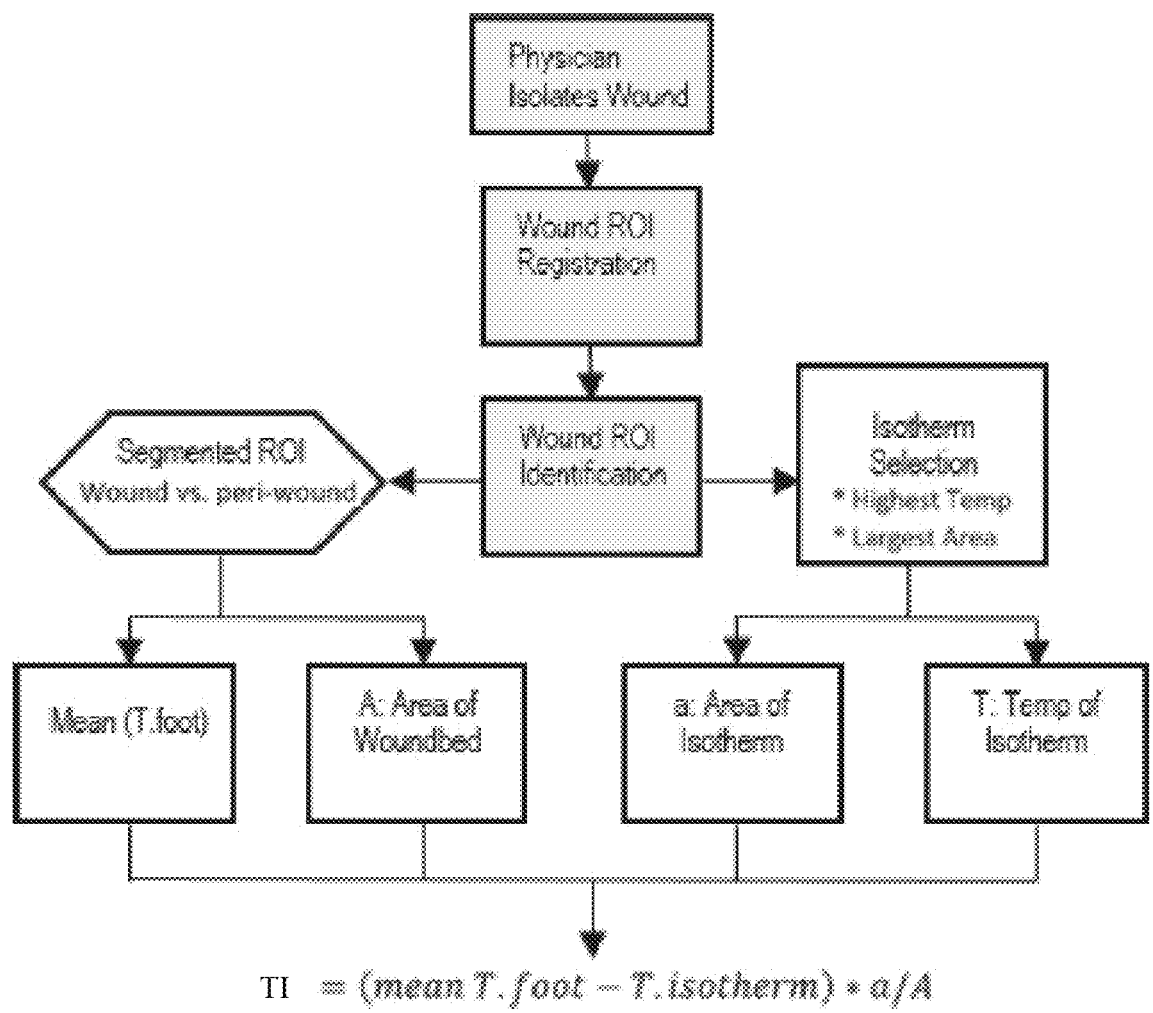
FIG. 13 is an automated ulceration risk assessment flowchart, according to one embodiment.

Referring now to FIG. 13, an automated ulceration risk assessment flowchart is shown. In this embodiment, the process involves four main steps, but other embodiments may include additional steps. In the first step, a physician selects a target wound area. In the second step, regions of interest (ROI's) are identified, where hot or cold spots could exist indicating inflammation, new ulceration, ulcer recurrence and potential skin breakdown. Gradient-based edge and contour plotting may be used in this step. In the third step, wound ulcer and peri-wound locations are identified within in the ROIs, as well as selection of isotherm candidates. In the fourth step, an ulceration risk is estimated by calculating the TI index of the ulcer, where $\Delta T$ is the difference between the isotherm and mean foot temperature, the area of the of the wound-bed (A) and area of the isotherm (a).

In one embodiment, to start the assessment process, a physician can use, e.g., a computer mouse and stylus to isolate wound ROIs. Next, the registration of ROIs can be performed. The identification of ROI features (i.e. area of wound ulcer, mean temperature, area of isotherms, and isotherm temperature) can be performed following ROI registration. The computation of the TI Index can be the final step for wound healing assessment.

Region of Interest Registration Algorithm and Analysis

In one embodiment, a computer-implemented algorithm can be used to identify and indicate inflammation and potential skin breakdown in a selected physiological region-of-interest (ROI), e.g., a hot- or cold-spot. The algorithm can include, without limitation: edge detection via Sobel edge (i.e. gradient-based) segmentation, Euclidean segmentation, or both. An exemplary approach to Sobel edge detection can be found in: Sharma, Achal et al., "Analysis of Sobel Edge Detection Technique for Face Recognition," *International Journal of Advanced Research in Computer Engineering and Technology*, vol. 4, issue 5, May, 2015. An exemplary Euclidean segmentation approach can be found in: N. Selvarasu et al., "Euclidean Distance Based Color Image Segmentation of Abnormality Detection from Pseudo Color Thermographs," *International Journal of Computer Theory and Engineering*, Vol. 2(4), August 2010, 1793-8201. Euclidean-based color image segmentation is a powerful image processing technique for identifying regions of interest with inflammation behavior. Euclidean distance segmentation analyzes IR imagery based on the RGB color model. Each RGB color pixel is a triplet of values, e.g., red, green and blue. Segmentation can provide optimal results in RGB color model when compared to other color models.

Figure 14:
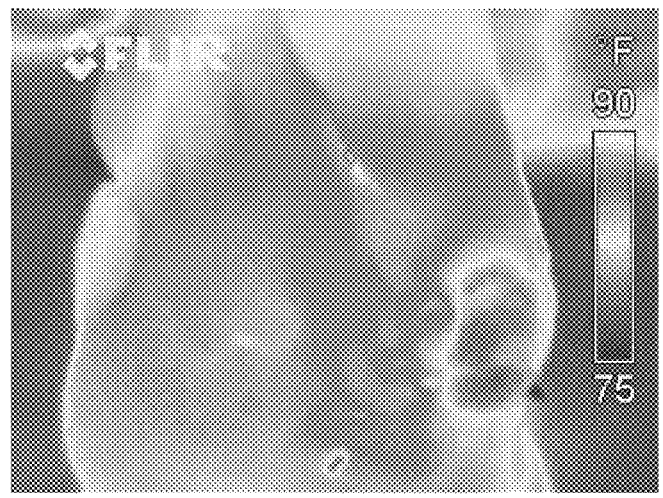
FIG. 14 is a thermal image of a subject's right foot.
Figure 15:
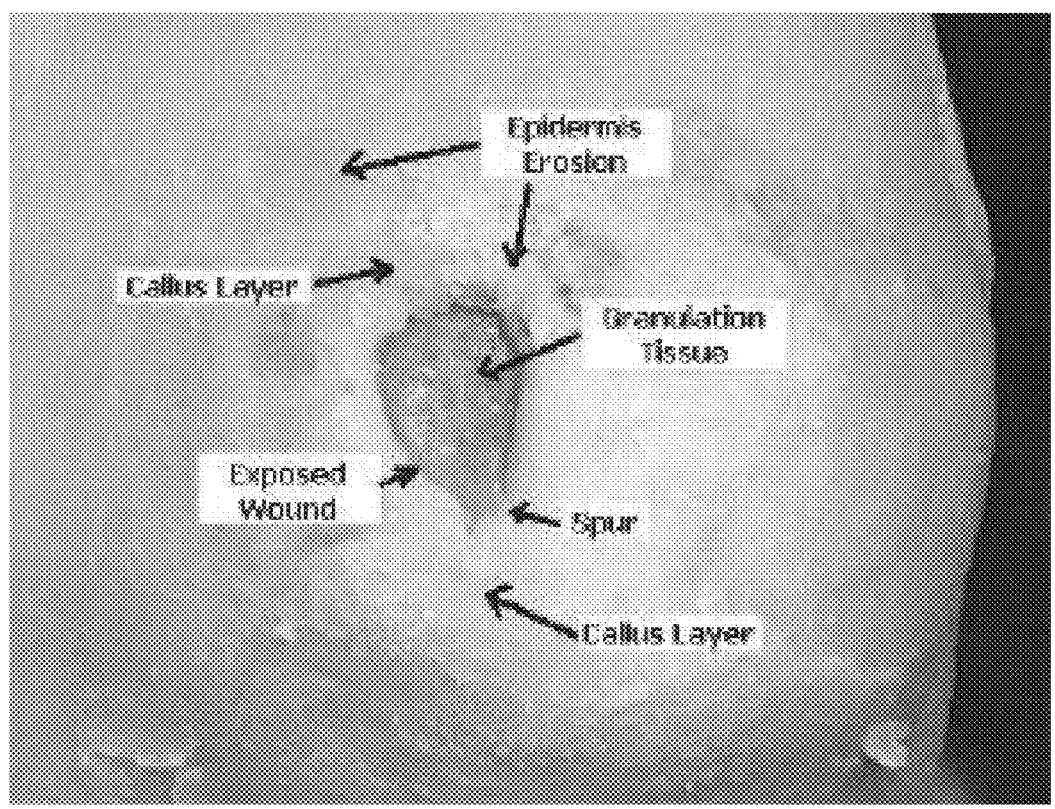
FIG. 15 is a color image corresponding with the thermal image of FIG. 14.
Figure 16:
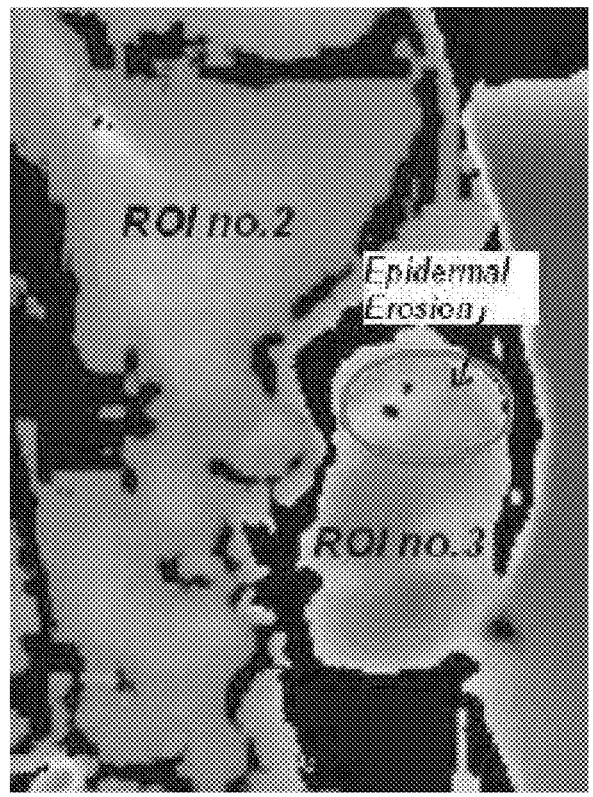
FIG. 16 illustrates identification of a ROI determined via Euclidean image processing, wherein two ROI's are highlighted: ROI 2 and ROI 3, according to one embodiment.

FIGS. 14, 15 and 16 illustrate Euclidean ROI image processing for a selected physiological area of 78 year old test subject (white male) with autonomic peripheral neuropathy (PN) without diabetes. (Bharara M., Schoess, J., Armstrong, D. G.; "Coming events cast their shadows before: detecting inflammation in the acute diabetic foot and the foot in remission," *Diabetes Metab Res. Rev.*, 2012, 28 Suppl 1:15-20.) In this example, FIG. 14 is a thermal image of the subject's right foot. A corresponding color (visible) image is shown in FIG. 15 with various regions of the wound and surrounding tissue abnormalities indicated. FIG. 16 illustrates the identification of a ROI determined via Euclidean image processing, wherein two ROI's are highlighted: ROI 2 and ROI 3.

In this example, the subject had been insensate in both feet since 2003 and has pulmonary fibrosis (oxygen-assisted). FIG. 16 highlights image processing results applying a Euclidean Distance Map (EDM) filter algorithm. The processed image reveals two different, key regions of interest within the mid-plantar region (i.e. red color) as ROI no. 2, and the foot ulcer site designated as ROI no. 3. The green-blue color of the ulceration site highlights a cooler temperature range from 78° F. to 80° F. due to circulatory inefficiency in the wound bed. The Euclidean image registers the distinct shape of the wound bed with a cooler temperature towards the center with upper and lower sub-regions. Two elongated semi-circular features are shown at the top of wound bed (highlighted in red circle) that illustrate the effect of epidermal erosion, wherein the outer skin layer is removed while the dermal layer remains intact.

Figure 17A:
FIG. 17A is a color image of a subject's left foot showing a diabetic ulcer.
Figure 17B:
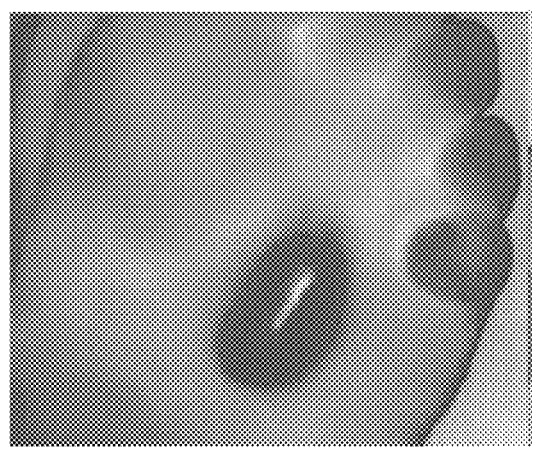
FIG. 17B is a thermal image of the same region of the foot as shown in FIG. 17A.

FIGS. 17A, 17B, 18A and 18B illustrate a process of wound identification and estimation of TI index, according to one embodiment for Subject 002 (Table 3). Subject 002 was a 41-year-old Latino female with a Left TMA ulcer; she is a type 2 diabetic with neuropathy. FIG. 17A is a color image of the left foot showing a diabetic ulcer. FIG. 17B is a thermal image of the same region of the foot. In this embodiment, the thermal image was decimated, e.g., down-sampled or down-converted from a color RGB format to a 16-bit grayscale image. Next, a 'Gaussian Blur' filter was applied to the 16-bit grayscale image to reduce noise and detail, and to enhance contour lines in subsequent image processing.

Figure 18:
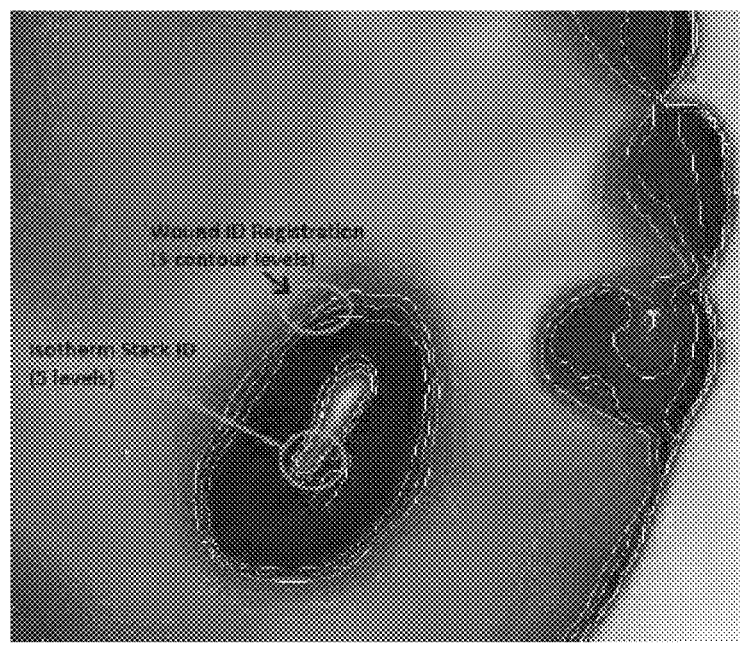
FIG. 18 is a processed image showing a wound area as a cooler, semicircular region surrounding an oblong isotherm in the center of the wound, itself displaying a warmer temperature within the wound, according to one embodiment.
Figure 19:
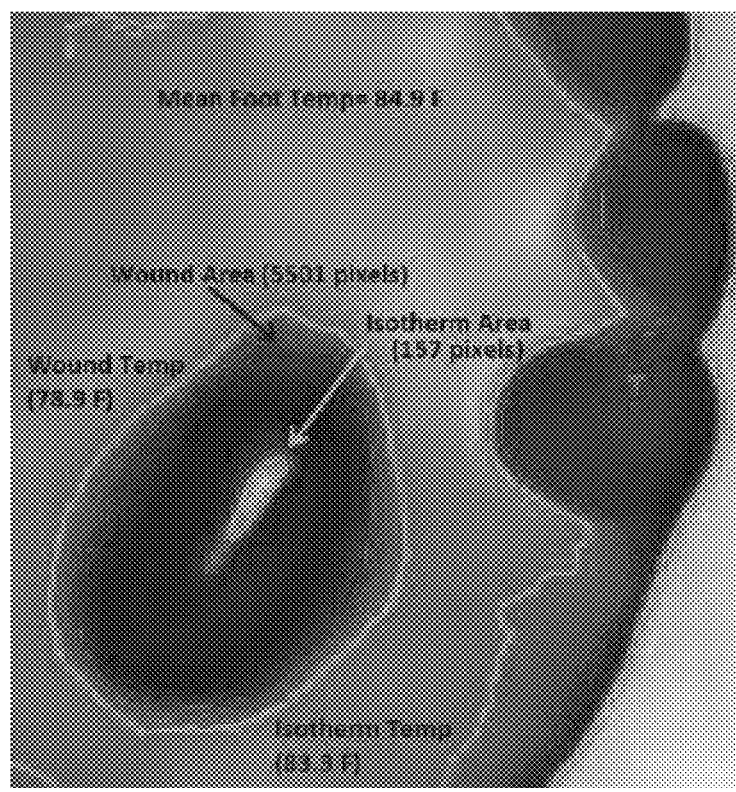
FIG. 19 is a processed image showing isotherms of a subject's foot.

Next, referring to FIGS. 18 and 19, in this embodiment, a contour plotting routine was applied to the (Gaussian) blurred, 16-bit grayscale image to identify inflammation patterns and isotherms in the image. Image isotherms, as the name implies, are image areas identified as having the same temperature. Isotherms can be isolated and identified by, e.g., assigning each isotherm in the image with a unique color. Referring to FIG. 18, the resultant processed image shows the wound area as a cooler, semicircular region surrounding an oblong isotherm in the center of the wound, itself displaying a warmer temperature within the wound. In this example, a series of five contour levels are highlighted at the edge of the wound area indicating a pattern of inflammation where healing is occurring. At the center of the wound, the isotherm stack is shown with five distinct levels of temperature variation.

In this embodiment, the thermal contour levels, temperature gradient, isotherm density, stack shape and isotherm area can be key features of the ROI for determining wound healing. In this example, the contours of the isotherms collectively define a topological temperature map, wherein the isotherm gradient reflects increasing or decreasing temperature. Isotherm density—e.g., spacing between isotherms—can indicate slope of the topological map or areas of steep or gradual temperature differences between ROI areas.

In one embodiment, the processed image can be reprocessed to quantify the isotherm area. The ROI's with the highest temperature and largest areas can be selected for further evaluation. In this example, and referring to FIG. 19, one isotherm area of interest is 157 pixels, corresponding to 83.3° F.; the wound area is determined to be 5501 pixels and 78.9° F.; and the mean foot temperature (utilizing the average of ten foot temperatures in the plantar of the foot was 84.9° F. In this embodiment, the processed image (FIG. 19) can be used to make a TI estimate. The TI index for this visit was +0.045, indicating a course of healing was occurring.

In various embodiments, the process of wound registration—i.e., selecting a wound region, and estimating isotherms and isotherm areas (areas bounded by isotherms) from a color or thermal photograph can be automated. The selection of which isotherms to identify and quantitate can also similarly be automated by, e.g., machine learning and artificial intelligence algorithms.

Another exemplary approach to image analysis is presented for "Subject 001" as referred to previously herein. In this example, thermal images were obtained for Subject 001 over ten distinct clinical visits. For each visit, the wound image was processed using Image. Image J is a Java-based image processing program developed at the National Institutes of Health and the Laboratory for Optical and Computational Instrumentation. All four visits were processed with the same image processing procedure and scored with the same settings using the Contour Plotter algorithm that defined the isotherm contour patterns. In this example, the image processing procedure included converting the RGB color image to 32 bit grayscale, applying a Gaussian blurring algorithm to reduce high frequency background noise and then applying the Contour Plotter algorithm. The Contour Plotter algorithm was configured to a set of individually pre-determined temperature levels, each level defining an isotherm temperature value.

Figure 20A:
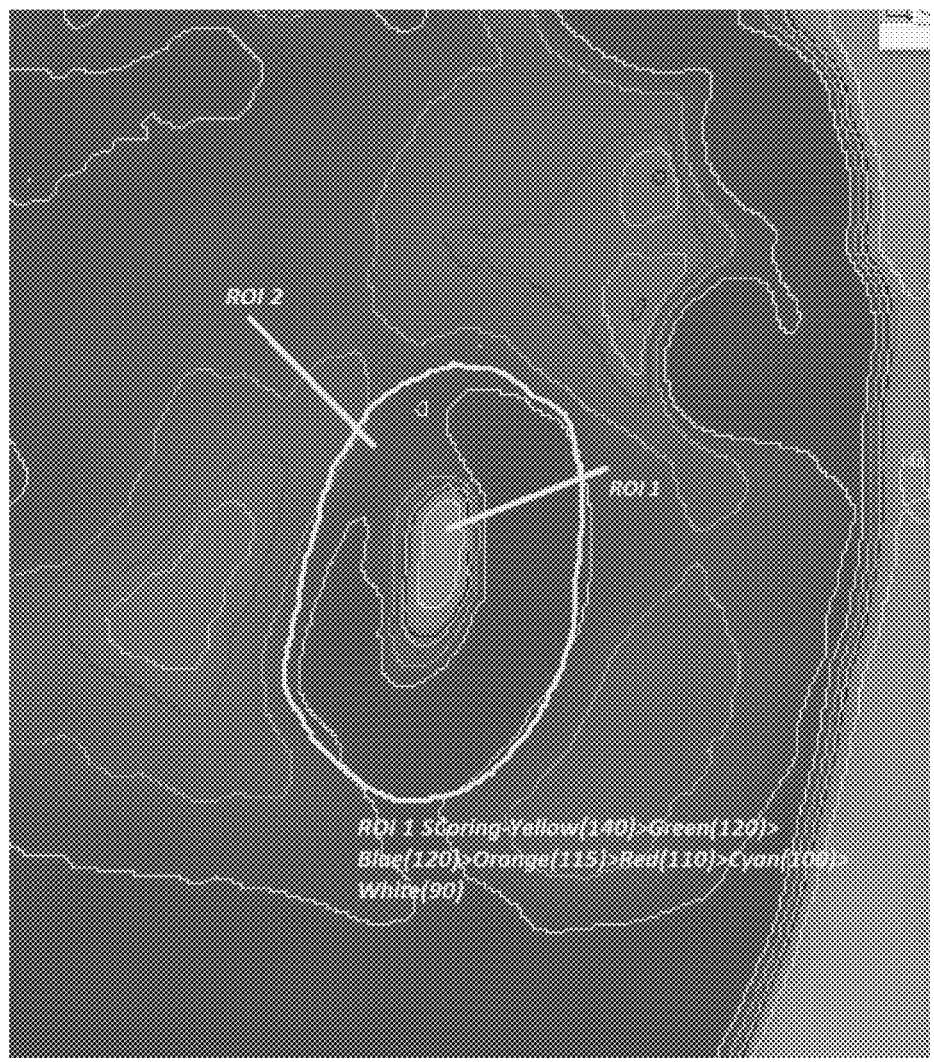
FIG. 20A is an image analysis of the thermal image of FIG. 20B, revealing a series of contour lines within the wound bed itself that defines the shape of the wound border, and the depth of the wound bed according to one embodiment.
Figure 20B:
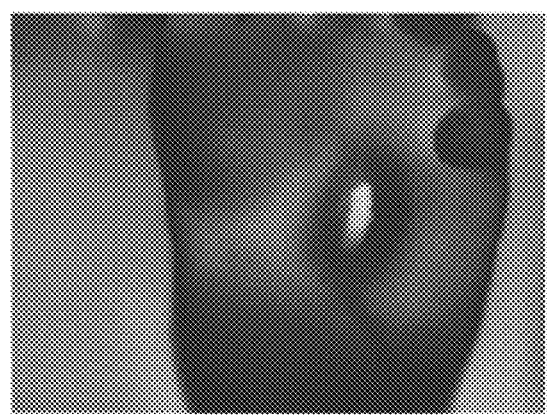
FIG. 20B is a thermal image of a wound bed on a subject's foot.

Referring now to FIG. 20A (visit 1), the initial image analysis of the thermal image (FIG. 20B) reveals a series of contour lines within the wound bed itself that defines the shape of the wound border, and the depth of the wound bed. In the examples that follow, a numerical 'level value' is indicated in parentheses. The level value is indicative of a temperature determined or detected by a particular pixel of the thermal imaging camera. While the values represent temperature, they should not be interpreted as actual temperature of the photographed surface. The highest measured temperature is in the center of the wound bed, shown in this example as the yellow contour line (level value 140). In this example, the temperature decreases as a 6-level isotherm stack from the center as: green (level value 130), to blue (level value 120) to orange (level value 115) to red (level value 110), to cyan (level value 100) to white (level value 90).

In this example, the contour levels are concentric. The spacing between contour levels is variable with more closely spaced lines on the right and left sides of the wound bed. The more closely spaced lines indicate the slope of wound bed cavity is steeper, illustrating wound depth. This is seen in the green, blue, red, and cyan stacks in particular. The depth of the wound can be measured over the course of healing, with a decrease in depth indicating wound healing, e.g., a depth healing index. The contour line or isotherm spacing indicates a gradient measure of profiling, e.g., a measure of wall slope. The stack of contour lines can be visualized as the thermal profile within the wound bed. In this example, each contour line outlines a specific amount of area within the wound bed. Each of these contour areas are regions of interest (ROIs) that can be added together to define a measure of healing, an ROI healing index. The sequence of warmer to cooler contour ROIs can indicate a hot spot in the center of the wound bed that gradually decreases in temperature progressing toward the wound bed edge. The contour line spacing may indicate that the degree of healing is greater at the edges, with wounds typically healing at the edges first and moving to the center; with the process of epithelialization occurring, epithelial cells at the edge of a wound proliferate almost immediately after injury to cover the denuded area. The hot spot ROI also may indicate increased blood flow into the wound bed to promote the healing process.

In one embodiment, a wound healing index can be derived by mathematical modeling of a contour map to determine regions of wound depth or elevation. For example, the contour lines of an isotherm map can be modeled analogously to topographical map, wherein isotherm or contour lines that are closer together indicate a steeper slope than those that are spaced further apart. The isotherms may indicate tunneling, which can indicate wound degradation, or the isotherms may indicate an elevated area, e.g., above or equal to the periwound area, that can indicate tissue granulation and healing. It should be understood that an isotherm map can include both wound depth and elevation corresponding to different portions of the wound that may be healing differently or at different rates.

In one approach, the contour map can be converted to a three-dimensional topographical map that allows the depth, elevation, or both of the wound bed to be determined qualitatively or quantitatively. Successive measurements of a wound bed over a period of time can be compared to determine if the depth of the wound bed is increasing (delayed wound healing), decreasing (wound healing), or staying the same (wound stasis). Successive measurements can also measure areas of elevation which can generally be considered a sign of wound healing. Other mathematical approaches to determine wound healing or delayed wound healing can be utilized, including measuring a gradient value, slope, or slope derivative of the contour or isotherm lines to allow a quantitative value to be assigned to the wound index.

Figure 21A:
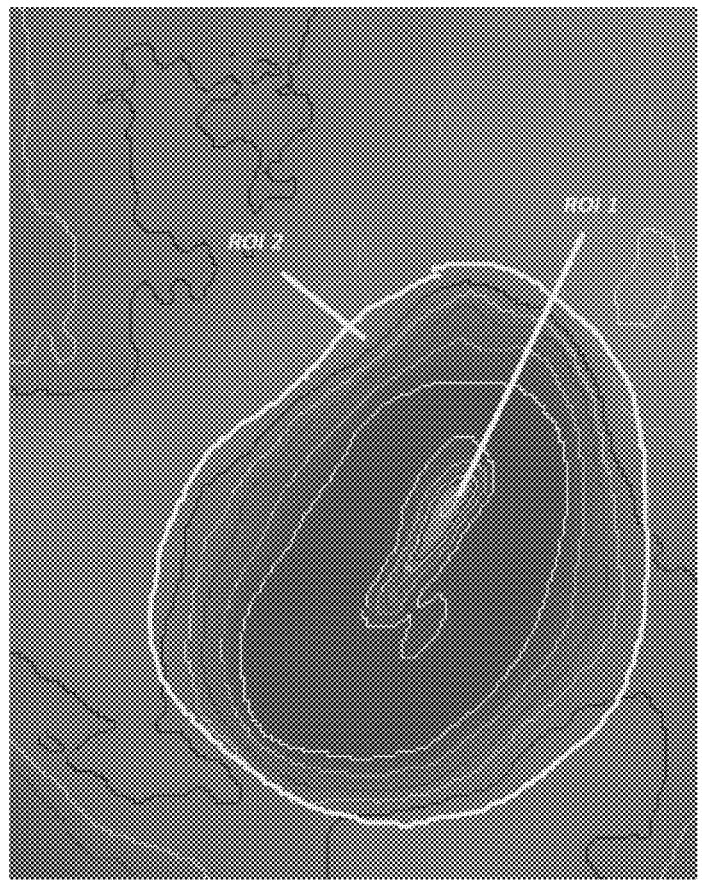
FIG. 21A is an image analysis of the thermal image of the wound bed of FIG. 21B.
Figure 21B:
FIG. 21B is a thermal image of a wound bed on a subject's foot.

Referring now to FIG. 21A (visit 2), the image analysis of the thermal image (FIG. 21B) reveals the wound bed shape has changed, to be narrower than that of visit 1 (FIGS. 20A, 20B), which may indicate wound closure and healing. The thermal profile of highest to lowest temperature with the stack of contours is shown, as with visit 1. The ROI area bordered by the yellow contour line (level value 140) is less area than visit 1. The contour lines clearly outline the elongated shape of the wound bed. The spacing of the contour lines on the right and left side of wound are more closely spaced, as with visit 1, indicating a depth of the wound; however, the spacing between lines has decreased, which may indicate the depth of the wound has decreased, and is healing. The 'green-blue-red-cyan' stack levels provide further physiological evidence; the peri-wound area of the wound is clearly highlighted, where the decrease in temperature indicates potential tissue hemorrhaging and capillary disruption. In one aspect, another index of healing would be the ratio of the peri-wound area to the wound bed area, the "wound area" index. The peri-wound border can be defined by the contour line profile of decreasing temperature (blue (level value 120), to orange (level value 115), to red (level value 110), to cyan (level value 100) to white (level value 90)).

Figure 22A:
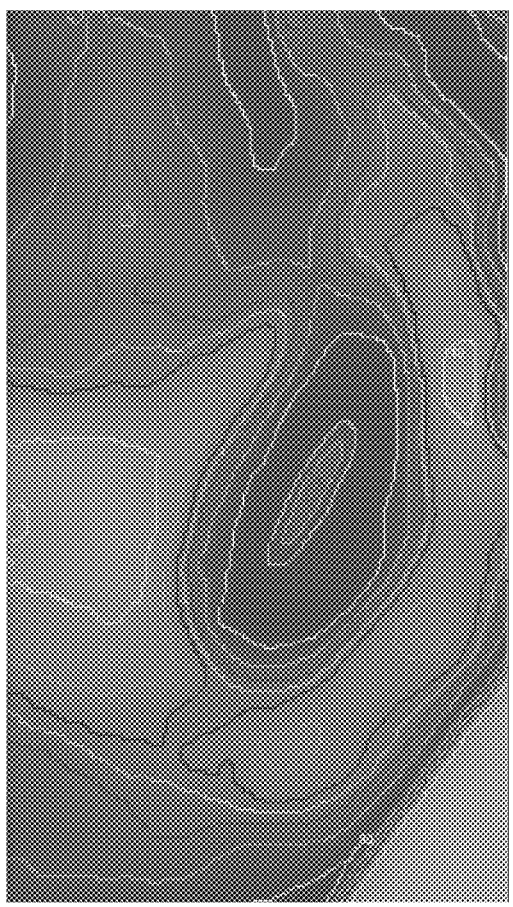
FIG. 22A is an image analysis of the thermal image of the wound bed shown in FIG. 22B according to one embodiment.
Figure 22B:
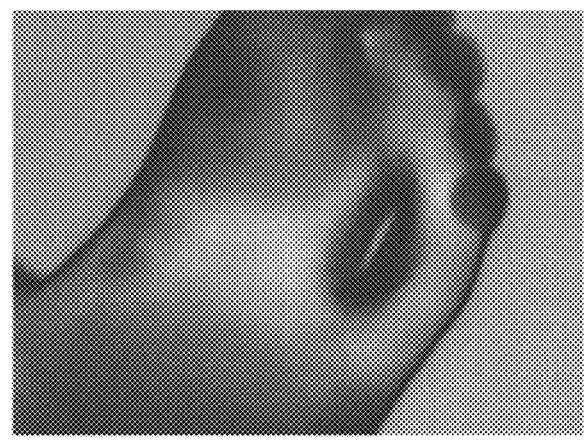
FIG. 22B is a thermal image of a wound bed.
Figure 22C:
FIG. 22C is a color image of the wound bed of FIG. 22B.

Referring now to FIGS. 22A-C, the image analysis (FIG. 22A) of the thermal image (FIG. 22B) is shown for the patient's eighth visit. (A photograph of the patient's foot is shown in FIG. 22C for reference.) In this series, the image analysis highlights a reduction of the number of contour lines to just a three level stack in the wound bed (red-cyan-white), with the absence of the higher temperatures. This result indicates a further reduction of wound depth and healing is occurring. Another evidence of healing is the decreasing gradient measurement between contour lines, i.e., the contour lines are further spaced apart than for the visit 1 or visit 2 series. The peri-wound area is also highlighted (orange-red-cyan-white) with increased spacing between contour lines. The ratio of peri-wound to wound bed (wound area index) has thus decreased.

Figure 23A:
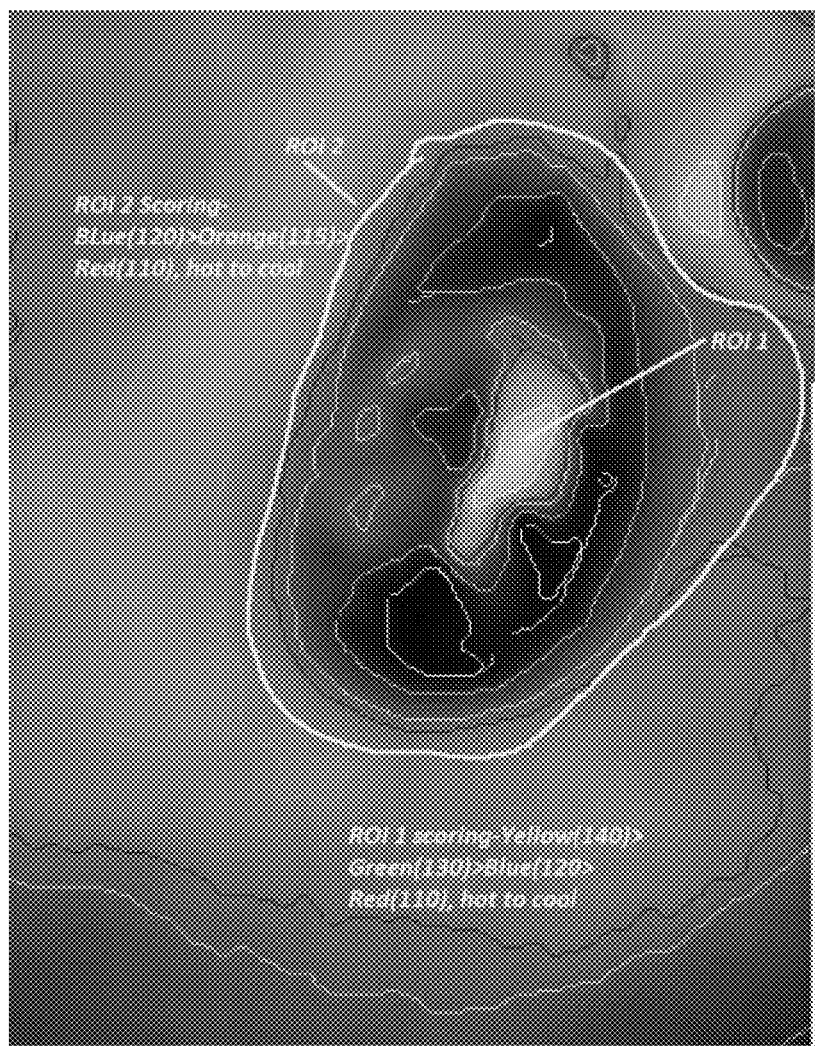
FIG. 23A is an image analysis of the thermal image of the wound bed shown in FIG. 23B according to one embodiment.
Figure 23B:
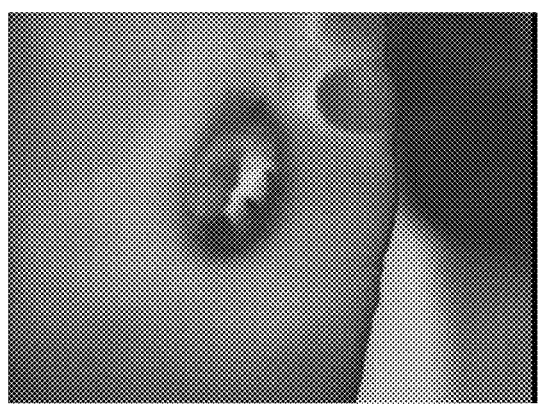
FIG. 23B is a thermal image of a wound bed.
Figure 23C:
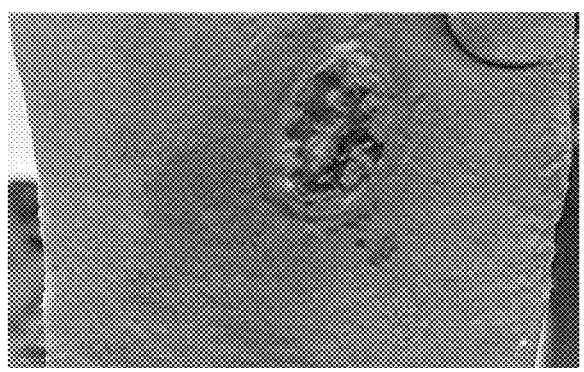
FIG. 23C is a color image of the wound bed of FIG. 23B.

Referring now to FIGS. 23A-C, the image analysis (FIG. 23A) of the thermal image (FIG. 23B) is shown for the patient's ninth visit, where it was observed that the wound had reopened. (A photograph of the patient's foot is shown in FIG. 23C for reference.) At the time of the visit, the wound bed appeared more irregular in shape, and has increased in temperature. This result was indicative of the wound opening up, resulting in a negative thermal index value. The gradient measure is lower between stacks, with greater inter-line spacing (contour levels). A four level isotherm stack (yellow (140)-green (130)-blue (120)-red (110)) indicated the thermal profile has reversed toward non-healing. The peri-wound area is clearly shown with four levels (blue (120)-orange (115)-red (110)-cyan (100)) indicating a hotter-to-cooler thermal pattern.

Figure 24A:
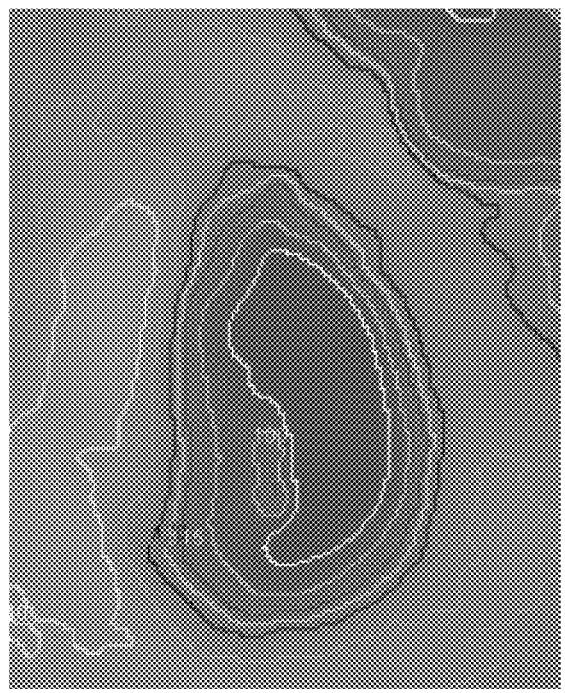
FIG. 24A is an image analysis of the thermal image of the wound bed shown in FIG. 24B according to one embodiment.
Figure 24B:
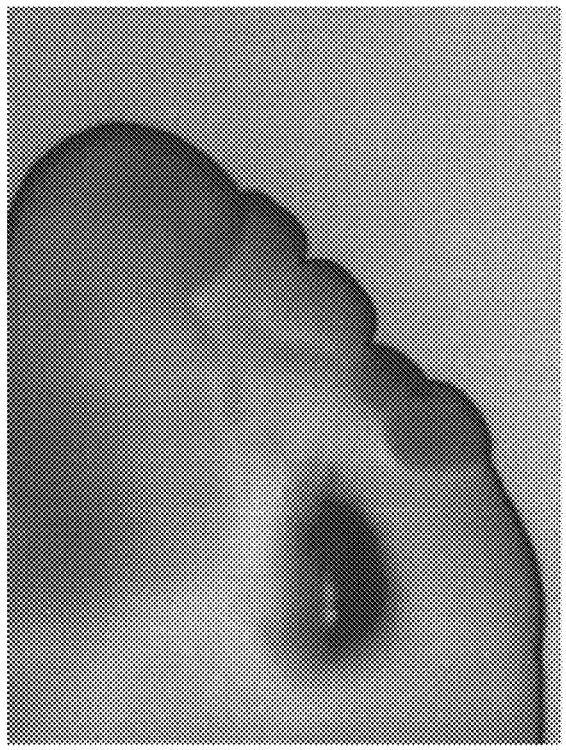
FIG. 24B is a thermal image of a wound bed.

Referring now to FIGS. 24A-B, the image analysis (FIG. 24A) of the thermal image (FIG. 24B) is shown for the patient's tenth visit. In this example, the image analysis indicates the wound bed has almost entirely disappeared. A double-ROI pattern is shown. A first, small area ROI (hot-spot) with a temperature level of 100 (cyan) is noticeable on the left side of the wound bed, indicating the remaining open cavity of the wound bed. A second ROI with a larger area exists to the right. The ROI area is indicated by a 4 level isotherm stack (white (90)-cyan (100)-red (110)-orange (115)). The 90- to 115 temperature pattern of the ROI indicates a cold spot exists with a negative transition from warmer (e.g., visit 9) to cooler (visit 10) with healing in progress. The hot spot area within the wound bed has also decreased from the previous visit, providing additional evidence of healing.

A number of illustrative embodiments have been described. Nevertheless, it will be understood that various modifications may be made without departing from the spirit and scope of the various embodiments presented herein. Any reference made herein or in the claims to living beings means animals of all conceivable types. Accordingly, other embodiments are within the scope of the following claims.

TABLE 1

Test population chart

| IR Eyes # | Subject No. | Gender | Age | Ethnicity | Diabetes Type | Neuropathy | Year Diagnosed | Foot | Location of Ulcer |
|---|---|---|---|---|---|---|---|---|---|
| 001 | 001 | Male | 33 | Undefined | Type 2 | Yes | — | Left | Left Mid Plantar Foot |
| 002elp | 002 | Female | 41 | Latino | Type 2 | Yes | — | Left | Left midfoot |
| 004 MK | 004 | Male | 61 | Native American | Type 2 | Not Specified | 1996 | Left | S/P Left TMA |
| 0055ARC | 005 | Female | 43 | African American | Type 2 | Not Specified | — | Right | Right lateral |
| JC006 | 006 | Male | 56 | African American | Type 2 | Not Specified | 1986 | Right | Distal Right Hallux |
| MT008 | 008 | Female | 58 | Latino | Type 2 | Yes | 1997 | Left | Lateral 5th MTH |
| MP009 | 009 | Male | 41 | Latino | Type 2 | Not Specified | 1996 | Left | Left 5th MTH, Lateral Border |
| JN011 | 011 | Male | 47 | Caucasian | Type 2 | Yes | 1998 | Right | Lateral Side |
| EO012 | 012 | Male | 70 | Caucasian | Type 2 | Yes | — | Left | Sub Left First APJ |
| RM13 | 013 | Female | 50 | Latino | Type 2 | Not Specified | 1996 | Left | Sub Left First APJ |
| 016KD | 016 | Female | 45 | Caucasian | Type 1 | Not Specified | 1985 | Left | Plantar 2nd MTH |
| 017LN | 017 | Male | 68 | Caucasian | Type 2 | Yes | — | Right | Right Plantar Midfoot |

TABLE 2

Subject 001 wound healing progression

| Subject ID | Age | Gender | Diabetes Type | Ethnicity | Year Diagnosed | Neuropathy | Foot | Location of Ulcer |
|---|---|---|---|---|---|---|---|---|
| 001 | 33 | Male | Type 2 | Not specified | Not Specified | Yes | Left | Mid Left Plantar |

| Visit Number | File | Date | Average Temp | Isotherm Area | Isotherm Temp | Woundbed Area | Woundbed Temp | Delta T | TI Calc | Isotherm |
|---|---|---|---|---|---|---|---|---|---|---|
| 1 | 623 | Sep. 27, 2016 | 83.1 | 593 | 86 | 5476 | 81.3 | −2.93 | −0.318 | warm |
| 2 | | Oct. 4, 2016 | | | | | | | | |
| 3 | 339 | Oct. 25, 2016 | 89.3 | 361 | 89.8 | 4353 | 87.7 | −0.444 | −0.0368 | warm |
| 4 | 327 | Nov. 18, 2016 | 84.7 | 298 | 83.7 | 7151 | 79.4 | 1.05 | 0.044 | cold |
| 5 | 215 | Dec. 2, 2016 | 87.9 | 115 | 87 | 1531 | 86.5 | 0.841 | 0.063 | cold |
| 6 | 203 | Dec. 28, 2016 | 90.4 | 253 | 90.7 | 5635 | 88.4 | −0.245 | −0.011 | warm |
| 7 | 207 | Jan. 5, 2017 | 87.5 | 352 | 85.4 | 4830 | 86.2 | 2.126 | 0.155 | cold |
| 8 | 319 | Jan. 13, 2017 | 86.7 | 191 | 83.6 | 4261 | 81.6 | 3.146 | 0.141 | cold |
| 9 | 207 | Jan. 20, 2017 | 88.2 | 205 | 89.6 | 9177 | 86.3 | −1.487 | −0.033 | warm |
| 10 | 543 | Feb. 3, 2017 | 91.1 | 189 | 88.2 | 3400 | 85.8 | 2.844 | 0.158 | cold |

TABLE 3

Subject 002 wound healing progression

| Subject ID | Age | Gender | Diabetes Type | Ethnicity | Year Diagnosed | Neuropathy | Foot | Location of Ulcer |
|---|---|---|---|---|---|---|---|---|
| 002 | 41 | Female | Type 2 | Latino married/no work | Not specified | Yes | Left | Left TMA site |

| Visit Number | File | Date | Average Temp | Isotherm Area | Isotherm Temp | Woundbed Area | Woundbed Temp | Delta T | TI Calc | Isotherm |
|---|---|---|---|---|---|---|---|---|---|---|
| 1 | 437 | Aug. 25, 2016 | 80.7 | 142 | 83.6 | 761 | 83.2 | −2.94 | −0.549 | warm |
| 2 | | Sep. 13, 2016 | | | | | | | | |
| 3 | | | | | | | | | | |
| 4 | 432 | Sep. 22, 2016 | 82.6 | 229 | 86.8 | 1160 | 85.9 | −4.2 | −0.829 | warm |
| 5 | 358 | Oct. 20, 2016 | 83.1 | 223 | 83.7 | 1300 | 83.95 | −0.653 | −0.112 | warm |
| 6 | 24632 | Oct. 26, 2026 | 79.7 | 325 | 81.5 | 2662 | 80.89 | −1.795 | −0.219 | warm |
| 7 | 545 | Nov. 1, 2016 | 84.1 | 120 | 83.8 | 1653 | 84.57 | 0.358 | 0.026 | cold |
| 8 | 233 | Nov. 8, 2016 | 87.8 | 89 | 87.8 | 1531 | 87.32 | −0.005 | −0.0003 | warm |
| 9 | 254 | Nov. 22, 2016 | 89.7 | 135 | 87.4 | 2716 | 88 | 2.347 | 0.117 | cold |
| 10 | 205 | Nov. 29, 2016 | 89.9 | 62 | 86.1 | 1936 | 87.8 | 3.806 | 0.122 | cold |
| 11 | 312 | Dec. 28, 2016 | 86.3 | 558 | 90 | 4850 | 88.8 | −3.741 | −0.43 | warm |
| 12 | 537 | Jan. 12, 2017 | 85.4 | 266 | 88.5 | 1485 | 87.7 | −3.125 | −0.559 | warm |
| 13 | 139 | Jan. 17, 2017 | 81.9 | 114 | 86.8 | 4653 | 84.1 | −4.851 | −0.119 | warm |

TABLE 4

Subject 005 wound healing progression

| Subject ID | Age | Gender | Diabetes Type | Ethnicity | Year Diagnosed | Neuropathy | Foot | Location of Ulcer |
|---|---|---|---|---|---|---|---|---|
| 005 | 43 | Female | Type 2 | African American nursing home/ no work | Not specified | unknown | Right | Right lateral |

| Visit Number | File | Date | Average Temp | Isotherm Area | Isotherm Temp | Woundbed Area | Woundbed Temp | Delta T | TI Calc | Isotherm |
|---|---|---|---|---|---|---|---|---|---|---|
| 1 | 407 | Sep. 13 2016 | 85 | 82 | 87.2 | 246 | 87.2 | −2.137 | −0.712 | warm |
| 2 | 3308 | Sep. 20, 2016 | 84.3 | 229 | 86.7 | 975 | 86.2 | −2.37 | −0.557 | warm |
| 3 | 457 | Sep. 30, 2016 | 87.3 | 171 | 89.3 | 586 | 88.9 | −2.047 | −0.598 | warm |
| 4 | 248 | Oct. 27, 2016 | 82.9 | 56 | 85.7 | 766 | 84.8 | −2.805 | −0.205 | warm |
| 5 | 300 | Dec. 13, 2016 | 86.2 | 432 | 86.7 | 1263 | 86.7 | −0.496 | −0.17 | warm |
| 6 | — | Jan. 5, 2017 | | | | | | | | Wound healed |

TABLE 5

Subject 011 wound healing progression

| Subject ID | Age | Gender | Diabetes Type | Ethnicity | Year Diagnosed | Neuropathy | Foot | Location of Ulcer |
|---|---|---|---|---|---|---|---|---|
| 011 | 47 | Male | Type 2 | Caucasian married/ teacher | 1998 | Yes | Right | lateral side |

| Visit Number | File | Date | Average Temp | Isotherm Area | Isotherm Temp | Woundbed Area | Woundbed Temp | Delta T | TI Calc | Isotherm |
|---|---|---|---|---|---|---|---|---|---|---|
| 1 | 355 | Nov. 21, 2016 | 89.6 | 5509 | 83.9 | 10195 | 84.9 | 5.7 | 3.079 | cold |
| 2 | 142 | Dec. 2, 2016 | 87.44 | 278 | 82.2 | 2917 | 84.7 | 5.204 | 0.495 | cold |
| 3 | 354 | Dec. 23, 2016 | 89.6 | 1948 | 85.2 | 8104 | 86.5 | 4.468 | 1.074 | dold |
| 4 | 137 | Jan. 13, 2017 | 89.9 | 299 | 94.6 | 3844 | 92.37 | −4.721 | −0.367 | warm |
| 5 | 436 | Feb. 3, 2017 | 86.5 | 532 | 88.7 | 5964 | 87.1 | −2.23 | −0.199 | warm |

| Day | Wound Area(pixels) | Isotherm Area(pixels) | Would Index |
|---|---|---|---|
| Subject No. 1 | | | |
| 0 | 1032 | 205 | 0.085 |
| 7 | 607 | 188 | −0.277 |
| 14 | 560 | 61 | −0.2015 |
| 35 | 38 | 12 | 0.368 |
| Subject No. 2 | | | |
| 1 | 1223 | 453 | −0.457 |
| 7 | 199 | 41 | −0.052 |
| 14 | 97 | 37 | −0.015 |
| 35 | 430 | 48 | 0.051 |
| Subject No. 3 | | | |
| 0 | 1775.00 | 322.00 | 0.0120 |
| 14 | 697.00 | 56.00 | −0.007 |
| 35 | 526.00 | 37.00 | 0.1782 |

What is claimed is:

1. A method for determining healing progress of a tissue injury, comprising:
   receiving a thermal image of a target wound area of a living subject from a thermal imaging system;
   processing said thermal image to construct an isotherm map of at least one selected area of said target wound area, said processing comprising
   converting said thermal image from a color image to a greyscale image;
   applying a digital filter to said greyscale image;
   applying a contour plotting algorithm to determine isotherms contained in said greyscale image; and
   assigning a contour level value correlated to a measured temperature value of each isotherm and optionally assigning a visual identifier to each isotherm;
   determining a depth, an elevation, or both of said selected area of said target wound area by measuring the spacing between adjacent isotherms of said isotherm map and deriving a healing index therefrom;
   comparing said healing index of said target wound area a first time and at least a second time, with a period of time intervening therebetween;
   determining a course of healing based on a comparison of said healing index between said first and said second time, to ascertain whether said tissue injury is progressing toward healing or delayed wound healing; and
   transmitting each determined healing index value to an output register.

2. The method of claim 1, wherein said healing index is derived by determining a numerical gradient, slope, or a derivative of said slope, of said spacing between adjacent isotherms.

3. The method of claim 1, wherein said period of intervening time is at least 24 hours.

4. The method of claim 1, wherein said healing index value is representative of healing progress of said tissue injury.

5. The method of claim 1, wherein said tissue injury is an ulcer.

6. The method of claim 1, wherein said applying a digital filter to said greyscale image comprises applying a Gaussian Blur filter.

7. The method of claim 1, further comprising decimating the bit depth of said thermal image.

8. The method of claim 1, wherein said thermal image is obtained by a thermal imaging camera and said output register is configured to transmit said healing index value to a remote computing system integral with a mobile health healthcare platform.

9. A method for determining a course of healing of a tissue injury, comprising:
  a) receiving a thermal image of a target wound area;
  b) digitally processing said thermal image to create an isotherm map comprising a plurality of isotherms, said plurality of isotherms defining a region of interest of said target wound area, wherein said digitally processing said thermal image comprises:
    converting said thermal image to a greyscale image;
    down-converting a bit depth of said greyscale image;
    applying a Gaussian Blur filter to said down-sampled image; and
    assigning a contour level value correlated to a measured temperature value of said isotherm and optionally assigning a visual identifier to each isotherm;
  c) determining a depth measurement, an elevation measurement, or both of said target wound area by measuring a gradient between at least two adjacent isotherms of said isotherm map representing a physiological depth or elevation of said target wound area;
  d) receiving a second, different and subsequent thermal image of said target wound area;
  e) repeating steps b) and c) with respect to said second thermal image;
  f) determining a course of healing by comparing differences between the determined depth or elevation of said target wound area of said first and said second thermal images; and
  g) transmitting the result of said determining step f) to an output register.

10. The method of claim 9, wherein the difference between the healing indexes of said first and said second thermal images can indicate a positive healing trajectory or a negative healing trajectory based on:
  whether a depth of said wound area is determined to be decreasing or increasing, respectively; or
  whether an elevation of said wound area is determined to be increasing or decreasing, respectively.

11. The method of claim 9, wherein said numerical index of each of said isotherms is correlated to a pixel-derived temperature value.

12. The method of claim 9, wherein said thermal image is obtained by a thermal imaging camera and said output register is configured to transmit said depth index value to a remote computing system integral with a mobile health healthcare platform.

13. A method for determining a course of healing of an ulcerative state in a living being, comprising:
  selecting a target wound area comprising an ulcer;
  obtaining a thermal image of said target wound area and deriving an isotherm map of said target wound area therefrom;
  identifying one or more regions of interest within said thermal map of said target wound area;
  determining a gradient or slope corresponding to a physiological depth or elevation of said ulcer by measuring a spacing between at least two adjacent isotherm lines within said thermal map and deriving a physiological depth or elevation of said target wound area therefrom;
  comparing said derived physiological ulcer depth of said target wound area at least twice, with an intervening time period of at least 24 hours therebetween;
  wherein a course of wound healing is represented by:
    a shallowing of said ulcer depth or an elevation of granulation equal to, or into the periwound area; and
  wherein a course of delayed wound healing is represented by a tunneling of said ulcer.

14. The method of claim 13, further comprising determining isotherms within a digitally-processed version of said thermal image.

15. The method of claim 14, wherein said digitally-processed version of said thermal image is obtained by gradient-based edge and contour plotting.

16. The method of claim 13, further comprising transmitting said physiological depth of said ulcer to a remote computing system integral with a mobile health healthcare platform.

17. The method of claim 13, wherein said derived physiological depth or elevation of said target wound area is transmitted to a server hosting an electronic health record system via an output register.

* * * * *